(12) United States Patent
Sinoncelli et al.

(10) Patent No.: US 8,314,045 B1
(45) Date of Patent: Nov. 20, 2012

(54) SOLID ACID CATALYST

(75) Inventors: Jacques Sinoncelli, Coronel Suarez (AR); Sergey V. Gurevich, San Mateo, CA (US)

(73) Assignee: Entreprises Sinoncelli S.A.R.L., Geneva (CH)

( * ) Notice: Subject to any disclaimer, the term of this patent is extended or adjusted under 35 U.S.C. 154(b) by 171 days.

(21) Appl. No.: 12/913,618

(22) Filed: Oct. 27, 2010

Related U.S. Application Data

(60) Provisional application No. 61/255,386, filed on Oct. 27, 2009.

(51) Int. Cl.
| | |
|---|---|
| *B01J 21/18* | (2006.01) |
| *B01J 23/00* | (2006.01) |
| *B01J 21/00* | (2006.01) |
| *C07C 2/02* | (2006.01) |
| *C07C 2/64* | (2006.01) |
| *C07C 15/067* | (2006.01) |
| *C07C 2/68* | (2006.01) |
| *C07C 5/22* | (2006.01) |
| *C07C 5/52* | (2006.01) |
| *C07C 15/12* | (2006.01) |
| *C07C 2/56* | (2006.01) |
| *C07C 45/00* | (2006.01) |
| *C07C 51/43* | (2006.01) |
| *C07C 63/04* | (2006.01) |
| *C11B 3/00* | (2006.01) |
| *C11B 7/00* | (2006.01) |
| *C11B 13/00* | (2006.01) |

(52) U.S. Cl. ........ 502/182; 502/180; 502/232; 585/375; 585/446; 585/467; 585/470; 585/709; 585/520; 568/314; 568/315; 568/322; 568/328; 554/176; 562/493

(58) Field of Classification Search .......... 502/180, 502/182, 232; 585/375, 446, 467, 470, 520, 585/709; 568/314, 315, 322, 328; 554/176; 562/493

See application file for complete search history.

(56) References Cited

U.S. PATENT DOCUMENTS

| | | | |
|---|---|---|---|
| 2,360,844 A | 11/1941 | Bradshaw et al. | |
| 4,270,929 A * | 6/1981 | Dang Vu et al. | 44/449 |
| 6,515,845 B1 * | 2/2003 | Oh et al. | 361/502 |

(Continued)

OTHER PUBLICATIONS

"Active solid acid catalysts prepared by sulfonation of carbonization-controlled mesoporous carbon materials," Rong Xing et al. Microporous and Mesoporous Materials 105 (2007), pp. 41-48.*

(Continued)

*Primary Examiner* — Patricia L Hailey
(74) *Attorney, Agent, or Firm* — Merchant & Gould P.C.

(57) ABSTRACT

A porous solid acid catalyst having high concentration of acidic sites and a large surface area includes a porous silica support and a sulfonated carbon layer disposed within the pores of the silica support. The catalyst, in certain embodiments, has a concentration of —$SO_3H$ groups of at least about 0.5 mmol/g and a predominant pore size of at least about 300 Å. The catalyst is used to catalyze a variety of acid-catalyzed reactions, including but not limited to alkylation, acylation, etherification, olefin hydration and alcohol dehydration, dimerization of olefin and bicyclic compounds, esterification and transesterification. For example, the catalyst can be used to catalyze esterification of free fatty acids (FFAs) and, in certain embodiments, to catalyze transesterification of triglycerides in fats and oils. The catalyst is prepared by impregnating a silica support with a phenol-containing material, processing the material to form a polymer, carbonizing the polymer to form a carbon layer within the silica support, and sulfonating the resulting carbon layer to form sulfonated carbon.

19 Claims, 11 Drawing Sheets

U.S. PATENT DOCUMENTS

| | | | |
|---|---|---|---|
| 6,812,187 B1 * | 11/2004 | Pak et al. ................... 502/180 |
| 6,924,407 B2 | 8/2005 | Subramaniam et al. |
| 7,718,155 B2 * | 5/2010 | Zhang et al. ............ 423/445 R |
| 7,854,913 B2 * | 12/2010 | Joo et al. ................. 423/445 R |
| 2004/0024267 A1 | 2/2004 | Dongare et al. |
| 2004/0260133 A1 | 12/2004 | Guillon et al. |
| 2005/0222457 A1 | 10/2005 | Okuhara et al. |
| 2006/0046925 A1 | 3/2006 | Schlitter et al. |
| 2006/0135823 A1 | 6/2006 | Jun et al. |
| 2008/0104885 A1 | 5/2008 | Sinoncelli et al. |
| 2008/0119664 A1 | 5/2008 | Sinoncelli et al. |
| 2008/0132733 A1 | 6/2008 | Manzer et al. |
| 2009/0099400 A1 | 4/2009 | Hamamatsu et al. |
| 2010/0312008 A1 * | 12/2010 | Kastner et al. .............. 560/231 |

OTHER PUBLICATIONS

"Sulfonated Ordered Mesoporous Carbon as a Stable and Highly Active Protonic Acid Catalyst," Xiqing Wang et al. Chem. Mater. 2007, 19, pp. 2395-2397.*

"Preparation of sulfonated ordered mesoporous carbon and its use for the esterification of fatty acids," Li Peng et al. Catalysis Today 150 (2010), pp. 140-146.*

"Amorphous Carbon Bearing Sulfonic Acid Groups in Mesoporous Silica as a Selective Catalyst," Kiyotaka Nakajima et al. Chem. Mater. 2009, 21, pp. 186-193.*

"Activation and deactivation characteristics of sulfonated carbon catalysts," Xunhua Mo et al. Journal of Catalysis 254 (2008), pp. 332-338.*

"Sulfonic-Functionalized Carbon Catalyst for Esterification of High Free Fatty Acid," Win Win Mar et al. Procedia Engineering 32 (2012), pp. 212-218.*

"Sulfonated ordered mesoporous carbon for catalytic preparation of biodiesel," Rui Liu et al. Carbon 46 (2008), pp. 1664-1669.*

"Role of silica template in the preparation of sulfonated mesoporous carbon catalysts," Jidon Janaun et al. Applied Catalysis A: General 394 (2011), pp. 25-31.*

"A Carbon Material as a Strong Protonic Acid," Michikazu Hara et al. Angew. Chem. Int. Ed. 2004, 43, pp. 2955-2958.*

"Versatile mesoporous carbonaceous materials for acid catalysis," Vitaly L. Budarin et al. Chem. Commun., 2007, pp. 634-636.*

"Synthesis of New, Nanoporous Carbon with Hexagonally Ordered Mesostructure," Shinae Jun et al. J. Am. Chem. Soc. 2000, 122, pp. 10712-10713.*

"Sulfonated mesoporous carbons as a solid sulfonic acid catalyst," Xiao Ning Tian et al. Studies in Surface Science and Catalysis, vol. 174, Part B, 2008, pp. 1347-1350.*

Molnar, A. "Nafion-Silica Nanocomposites: A New Generation of Water-Tolerant Solid Acids of High Efficiency", Current Organic Chemistry, vol. 12, 2008, pp. 159-181.

Kumar, P. et al. "Alkylation of Raffinate II and Isobutane on Nafion Silica Nanocomposite for the Production of Isooctane", Energy & Fuels, vol. 20, 2006, pp. 481-487.

Sarsani, V. et al. "Isobutane/butane alkylation on microporous and mesoporous solid acid catalysts: probing the pore transport effects with liquid and near critical reaction media", Green Chem., vol. 11, 2009, pp. 102-108.

Heidekum, A. et al. "Nafion/Silica Composite Material Reveals High Catalytic Potential in Acylation Reactions", Journal of Catalysis, vol. 188, 1999, pp. 230-232.

* cited by examiner

SOLID ACID CATALYST

This application claims benefit of Ser. No. 61/255,386, filed Oct. 27, 2009 in United States and which application is incorporated herein by reference. To the extent appropriate, a claim of priority is made to the above disclosed application.

FIELD OF THE INVENTION

The invention relates generally to solid acid catalysts, and to methods of using such catalysts in acid-catalyzed reactions, such as alkylation, acylation, etherification, dimerization, olefin hydration and alcohol dehydration, fatty acids esterification and transesterification reactions.

BACKGROUND OF THE INVENTION

Stable non-hazardous solid acid catalysts are widely sought after as replacements for liquid acid catalysts, such as sulfuric, hydrofluoric, and nitric acids. Solid acid catalysts can be used as heterogeneous catalysts in liquid-phase reactions, and are advantageous because they can be easily separated from liquid reaction mixtures. In addition, in view of corrosive and toxic nature of commonly used liquid acids, the environmentally benign non-corrosive solid acids appear particularly attractive. A variety of solid acids have been developed to address these needs, including sulfonated zirconia, $ZrO_2/WO_3$ catalyst, zeolites, acidic ion-exchange resins, and silica-supported Nafion® acid resin (e.g., SAC-13, commercially available from Sigma-Aldrich, Milwaukee, Wis.). However, activities and stabilities of these catalysts are often insufficient for commercial use.

A solid acid catalyst could be useful in the process of fatty acid methyl ester manufacturing. Fatty acid methyl esters have acquired considerable commercial significance as starting materials for production of biodiesel fuels, fatty alcohols and other oleochemical products, such as ester sulfonates, and fatty acid alkanolamides. Industrially, fatty acid methyl esters are produced mainly by catalytic transesterification (alcoholysis) of fatty acid triglyceride mixtures, obtained from fats and oils of vegetable and animal origin. However, natural fats and oils almost always contain considerable amount of free fatty acids (FFAs), which readily form soaps upon exposure to alkaline reagents commonly used during transesterification. Formation of soaps significantly complicates isolation of resulting methyl esters, and therefore should be avoided. Reduction of FFA content can be performed, for example, by converting the FFAs into the corresponding alkyl or glycerin esters in a preliminary pre-esterification reaction.

Recently, a number of solid catalysts were suggested for FFA pre-esterification, including acid resins and silica-supported Nafion® acid resin. However, acid resins have low thermal stability, poor mechanical properties, and are also subject to swelling. SAC-13 catalyst has relatively low activity and relatively low thermal stability.

SUMMARY

A new class of heterogeneous solid acid catalysts, suitable for catalyzing a variety of acid-catalyzed reactions is provided. The present solid acid catalysts are characterized by high concentration of acidic sites and large surface area. The catalysts, in certain embodiments, have high thermal stability, high catalytic activity, and exhibit little or no swelling upon exposure to liquids at high temperature.

In one aspect, a porous solid acid catalyst is provided, where the catalyst includes a support having a porous silica network and a sulfonated carbon layer disposed within the porous silica network. The catalyst, in certain embodiments, is characterized by a high concentration of —$SO_3H$ groups of at least about 0.5 mmol/g, and by relatively large pores, with a predominant pore size of at least about 300 Å. In certain embodiments the solid acid catalyst has a concentration of —$SO_3H$ groups of at least about 0.7 mmol/g, e.g., at least about 1 mmol/g and higher. The predominant pore size, in certain embodiments, is at least about 350 Å, e.g., at least about 400 Å.

In certain embodiments, the present catalysts are characterized by large surface area, with Brunauer-Emmett-Teller (BET) parameter reaching 50 $m^2/g$ and greater, such as 100 $m^2/g$ and greater.

In some aspects, a method for carrying out an acid-catalyzed reaction is provided. The method includes (a) contacting the present solid acid catalyst with a starting material of an acid-catalyzed reaction under conditions that are suitable for effecting the acid-catalyzed transformation, and (b) recovering a product of the acid-catalyzed transformation.

In certain embodiments, a method of performing an alkane alkylation is provided, wherein the method includes contacting the present solid acid catalyst with a starting material including an alkane and an alkene under conditions suitable to effect alkane alkylation; and recovering a product including an alkylated alkane. For example, in an embodiment the method includes contacting the catalyst with a mixture including isobutane and but-2-ene to form one or more octanes; and subsequently recovering the one or more octanes. The reaction can provide high-grade gasoline components (isooctanes).

The present catalysts can be used for catalyzing a variety of acid-catalyzed reactions, which include but are not limited to alkylation, acylation, etherification, olefin hydration, and alcohol dehydration reactions. The present catalysts are effective in catalyzing esterification reactions, and transesterification reactions under certain conditions. The present solid acid catalyst has high activity in catalyzing esterification of fatty acids with monohydric alcohols. For example, the present solid acid catalyst is active in esterification of fatty acids with methanol. Activities of the present solid acid catalyst in certain embodiments reach at least about 150 mL/hours·g for esterification of lauric acid with methanol in liquid phase at 80° C. In certain embodiments, catalytic activities of the present solid acid catalyst for esterification are at least two times or at least three times greater than activities of conventional SAC-13 catalyst, measured under identical conditions. At high temperatures, e.g., at 120° C. activities of the present solid acid catalysts are often at least 10 times greater than activity of the SAC-13.

Further, in an embodiment, the present solid acid catalyst has good thermal stability and exhibits advantageously small volumetric size increase (swelling) upon exposure to esterification reaction mixtures. For example, in an embodiment, the present solid acid catalyst retains at least about 30% of its initial esterification activity upon exposure to an esterification reaction mixture at 120° C. for 12 hours. Further, in an embodiment, the present solid catalyst exhibits less than about 20% swelling, for example, less than 5% swelling upon exposure to a liquid esterification reaction mixture for 12 hours at 80° C.

The present solid acid catalyst is also active in catalyzing FFA esterification with monohydric alcohols in biodiesel feedstocks containing FFAs and triglycerides.

In an embodiment, the present solid acid catalyst is active in catalyzing transesterification reactions, specifically transesterification of triglycerides with monohydric alcohols, such as methanol or ethanol. For example, in an embodiment, the present solid acid catalyst is active in catalyzing transesterification of triglycerides contained in biodiesel feedstocks, such as fats and oils.

In another aspect of the invention, a method of making the present solid acid catalyst is provided. The method includes: (a) impregnating a porous silica support with a phenol-containing material; (b) processing the phenol-containing material to form a polymer containing aromatic groups, wherein the polymer resides within the pores of the porous silica support; (c) carbonizing the polymer by exposing it to high temperature in a non-oxidizing atmosphere to form a carbon layer within the pores of the silica support; and (d) treating the obtained carbonized partially prepared catalyst with a sulfonating agent to form a sulfonated carbon layer within the porous silica support. Further, in an embodiment, the method also includes washing the partially formed catalyst to remove sulfate ions, and subsequently drying the structure.

A variety of silica supports can be used for preparation of the present solid acid catalyst. In an embodiment, a silica with a relatively large pore size, e.g., silicas having a predominant pore size of at least about 300 Å, for example, at least 400 Å are used. Suitable materials include those with predominant pore sizes in the range of between about 300 Å and about 5,000 Å. Further, silica supports with large surface area, e.g., with a BET parameter of at least about 100 m$^2$/g are suitable. In some implementations, the silica support is water-resistant silica. Silica supports encompass porous silicas, such as silica gel. It is understood that conventional silica-containing glasses and silicates known in the art, are considered non-porous, for the purposes of this application.

The phenol-containing material used for silica impregnation can include monomers, oligomers or polymers. For example, in an embodiment, one or more monomers, such as phenol and formaldehyde are introduced into the silica support and are polymerized within the support. In an embodiment, a phenol-formaldehyde resin (e.g., low- or high-molecular weight polymers or oligomers) are introduced into the support and are subsequently cured to form a cross-linked polymer.

In an embodiment, a phenol-formaldehyde epoxy resin (e.g., oligomers or low molecular weight polymers) is introduced into the support and is cured, for example, either chemically or thermally. For example, in an embodiment, the present method includes contacting the porous silica support with a phenol-formaldehyde epoxy resin and with a curing agent and allowing the resulting mixture to cure for a period of time. In an embodiment, the present method includes contacting the silica support with a solution containing a phenol-formaldehyde epoxy resin and 2-ethyl-4-methylimidazole curing agent in ethyl acetate solvent. A variety of phenol-formaldehyde epoxy resins can be used, including resins containing bisphenols A and F and novolac resins. In an embodiment, the phenol-formaldehyde epoxy resin is cured thermally, e.g., by heating the structure at a suitable temperature for a period of time to form a polymer.

Upon formation of a polymer, the structure is carbonized, e.g., by heating at a temperature of at least about 200° C. for at least one hour in inert gas atmosphere, and is then sulfonated by contacting the structure with a sulfonating agent, such as sulfuric acid to form a layer of sulfonated carbon within the porous silica network.

The present solid acid catalyst, formed by this method, exhibits high density of SO$_3$H groups, high activity in catalyzing esterification reactions, high thermal stability, and little or no swelling.

In another aspect of the invention, a method for performing esterification is provided. The method includes contacting a mixture including an acid and an alcohol with a porous solid acid catalyst, under conditions suitable for forming an ester. The present solid acid catalyst, as described above, includes a support including a porous silica network; and a sulfonated carbon layer disposed within the porous silica network, wherein the solid acid catalyst has a concentration of —SO$_3$H groups of at least about 0.5 mmol/g, and a predominant pore size of at least about 300 Å. In an embodiment, the present method includes contacting a mixture containing a fatty acid and a monohydric alcohol, such as methanol, ethanol, and propanol, with the present solid acid catalyst. In an embodiment, the mixture further contains triglycerides. For example, in an embodiment, the mixture includes a biodiesel feedstock including a fat or an oil and at least 0.5 weight % of FFAs.

In another aspect of the invention, a method for performing transesterification is provided. This method includes contacting a mixture including a first ester and an alcohol with present solid acid catalyst, to form a second ester, wherein the catalyst includes a support including a porous silica network and a sulfonated carbon layer disposed within the porous silica network, wherein the solid acid catalyst has a concentration of —SO$_3$H groups of at least about 0.5 mmol/g, and a predominant pore size of at least about 300 Å. For example, transesterification of triglycerides with monohydric alcohols, such as methanol, ethanol, or propanol can be performed. In certain embodiments, the mixture includes an alcohol and an unprocessed or a pre-processed biodiesel feedstock including a fat or an oil.

In another aspect of the invention, a method for processing a biodiesel feedstock including a triglyceride and an FFA is provided. This method includes: (a) contacting the feedstock with a monohydric alcohol and with the present solid acid catalyst, under conditions suitable for esterification of the free fatty acid; and (b) contacting the mixture obtained after (a) with a monohydric alcohol and with a second catalyst under conditions suitable for transesterification of the triglyceride. The second catalyst, in an embodiment, is a basic catalyst. In an embodiment, the second catalyst is a solid acid catalyst, e.g., the present solid acid catalyst. For example, in an embodiment the present solid acid catalyst when employed for esterification of FFA and transesterification of triglyceride includes a support including a porous silica network; and a sulfonated carbon layer disposed within the porous silica network, wherein the solid acid catalyst has a concentration of —SO$_3$H groups of at least about 0.5 mmol/g, and a predominant pore size of at least about 300 Å. When solid acid catalyst of the invention is used for both esterification and transesterification, its composition need not necessarily be the same for both reactions.

In certain embodiments the method of processing biodiesel feedstock further includes removing water from the mixture obtained after esterification reaction and prior to performing transesterification of triglycerides. Water can be removed, for example, by distillation.

In another aspect, a method for processing a biodiesel feedstock including a triglyceride is provided. This method includes contacting the feedstock with a monohydric alcohol and with the present solid acid catalyst under conditions suitable for transesterification of the triglyceride, wherein the present solid acid catalyst includes a support including a porous silica network; and a sulfonated carbon layer disposed within the porous silica network, wherein the present solid acid catalyst has a concentration of —SO$_3$H groups of at least about 0.5 mmol/g, and a predominant pore size of at least about 300 Å.

In yet another aspect a reactor for performing esterification or a transesterification reaction is provided. The reactor includes walls defining a reactor chamber; an inlet for introducing reactants into the reactor chamber; and the present solid acid catalyst disposed within the reactor chamber, wherein the present solid acid catalyst includes: (a) a support including a porous silica network; and (b) a sulfonated carbon layer disposed within the macroporous silica network, wherein the present solid acid catalyst has a concentration of —SO$_3$H groups of at least about 0.5 mmol/g, and a predominant pore size of at least about 300 Å.

These and other features and advantages of the invention will be described in more detail below with reference to the associated drawings.

DETAILED DESCRIPTION OF A PREFERRED EMBODIMENT

Figure 1:
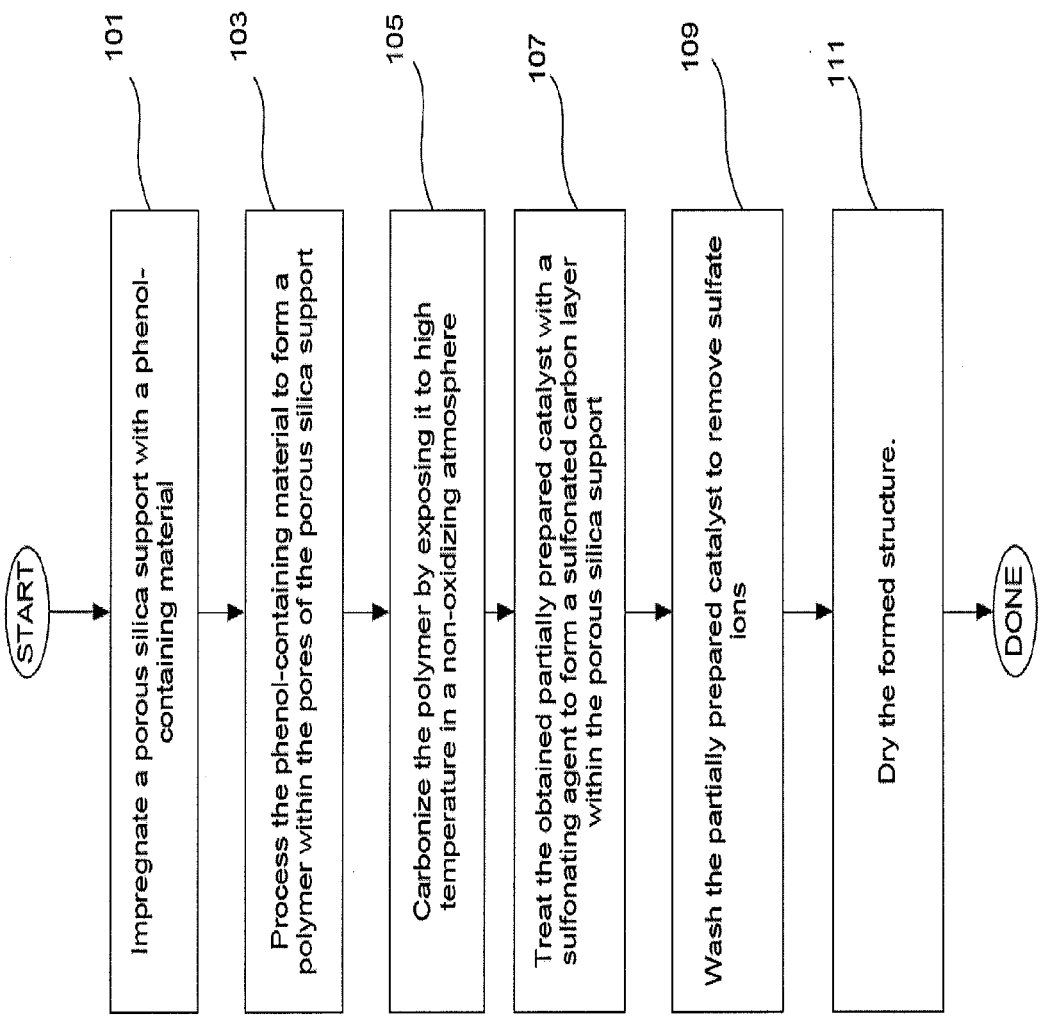
FIG. 1 is a process flow diagram for a method of making a solid acid catalyst in accordance with certain embodiments provided herein.

According to embodiments described herein, a new highly active solid acid catalyst having a porous structure, large surface area and high concentration of acidic sites is provided. In an embodiment, the present solid acid catalyst is further characterized by high thermal stability and, unlike solid acid resins, is not prone to swelling upon exposure to liquid reaction mixtures at high temperature. The present solid acid catalyst includes, in an embodiment, a porous silica support and a sulfonated carbon layer disposed (or residing) within the pores of the silica support. The present solid acid catalyst, in certain embodiments, has a concentration of —SO$_3$H groups of at least about 0.5 mmol/g and a predominant pore size of at least about 300 Å. In general, other supports having sufficient porosity (preferably with predominant pore size of at least about 300 Å but typically not greater than 5,000 Å) can be used. Such supports include without limitation porous titania and zirconia. In an embodiment, suitable supports should be able to withstand sulfonation conditions used during catalyst preparation (e.g., treatment with sulfuric acid).

The present solid acid catalyst can be used to catalyze acid-catalyzed reactions, including but not limited to, alkylation, acylation, etherification, isomerization, dimerization, olefin hydration, alcohol dehydration, esterification and transesterification reactions. For example, the present catalyst can be used to catalyze alkane/alkene alkylation. In an embodiment, the present solid acid catalyst can be used to catalyze esterification of free fatty acids (FFAs). In an embodiment, the present solid acid catalyst can be used to catalyze transesterification of triglycerides in fats and oils. The present solid acid catalyst can be prepared by impregnating a silica support with a phenol-containing material, processing the material to form a polymer, carbonizing the polymer to form a carbon layer within the silica support, and sulfonating the resulting carbon layer to form sulfonated carbon.

In an embodiments, the present solid acid catalyst consists essentially of a support that includes a porous silica network or is itself a porous silica network, and a sulfonated carbon layer disposed within the pores of the silica network. In certain embodiments the use of macroporous silica as support is preferred.

DEFINITIONS

As used herein, "sulfonated carbon layer" is a layer including carbon and —SO$_3$H groups, wherein the layer may further include hydrogen, and, optionally, other elements. For example, sulfonated partially carbonized hydrocarbons are within the scope of "sulfonated carbon layer". However, intact (non-carbonized) sulfonated organic molecules, e.g., sulfonated polymers such as sulfonated tetrafluoroethylene-based polymers (Nafion®) are not included within the scope of "sulfonated carbon layer".

As used herein, "carbonization" is a process of increasing carbon content in a material, which in certain embodiments is performed by pyrolysis of a carbon-containing material (e.g., organic polymer) in a non-oxidizing atmosphere. Partial carbonization (which does not include complete removal of all H atoms from the carbonized material) is encompassed and preferred in many embodiments.

As used herein, "a phenol-containing material" includes a material including structure I

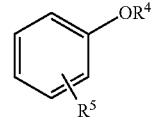

wherein $R^4$ is hydrogen or an organic substituent (e.g., an epoxyalkyl), and wherein $R^5$ is one or more optional substituents. The phenol-containing material can include monomers, oligomers, or polymers. Examples of phenol-containing materials include without limitation phenol-formaldehyde resins (e.g., bakelite and novolac), phenol-formaldehyde epoxy resins such as bisphenol A and bisphenol F-containing epoxy resins, and novolac epoxy resins such as oligomer II

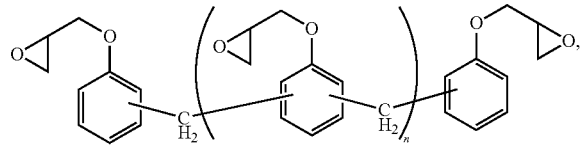

where n can range from 0 to 25.

As used herein, "esterification reaction" refers to a reaction between an acid and an alcohol, which results in formation of an ester (e.g., equation 1, forward reaction, where $R^1$ and $R^2$ are organic substituents, such as alkyls, alkenyls, alkynyls, aryls, etc.).

In general, an esterification reaction is not limited to the use of organic starting materials but also encompasses esterification of inorganic acids, e.g., boric acid, etc.

As used herein, "ester hydrolysis reaction" refers to a reaction of an ester with water or a base resulting in formation of an acid (or its salt) and an alcohol (e.g., equation 1, reverse reaction).

Unless explicitly stated to the contrary, the present solid acid catalyst can be applied both in connection with the forward reaction as shown above (i.e. esterification) or alternatively in connection with the reverse reaction as shown above (i.e. ester hydrolysis). The equilibrium of reaction (1) can be shifted in the required direction, for example, through judicious choice of temperature and pressure, removal of reaction products, use of excesses of starting materials, etc.

As used herein, "transesterification reaction" refers to a reaction between an ester and an alcohol to form another ester. For example, transesterification of a triglyceride (a glycerol ester) with methanol is illustrated by equation (2) (forward reaction).

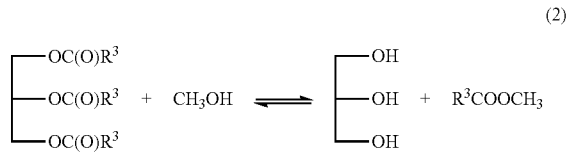

wherein $R^3$ is an organic substituent, such as an alkyl or alkenyl. It is noted that $R^3$ moieties need not necessarily be identical in one triglyceride molecule.

As used herein, "fatty acid" refers to a carboxylic acid with an aliphatic (saturated or unsaturated) chain, the acid having at least four (such as at least eight) carbon atoms. Examples of fatty acids include but are not limited to caprylic, lauric, stearic, palmitic, linoleic, linolenic, and oleic acids.

As used herein, "monohydric alcohol" refers to an alcohol containing one —OH group. Examples of monohydric alcohols include but are not limited to methanol, ethanol, propanol, isopropanol, and n-butanol, sec-butanol, and tert-butanol.

As used herein, "macroporous silica" refers to a porous silica material having predominant pore size about 400-500 Å.

As used herein, the term "about" modifying, for example, a quantity or size of, a feature of the present invention refers to variation in the numerical quantity that can occurs, for example, in making and using solid acid catalysts in the real world; through inadvertent error in such making or using; through differences in the manufacture, source, or purity of the components employed to make the catalyst or to carry out the methods; and the like. Whether or not modified by the term "about", the claims include equivalents to the quantities.

The Present Catalyst Compositions

The present solid acid catalyst can be a porous catalyst that includes a support including a porous silica network and a layer of sulfonated carbon disposed in the pores of the silica network. As previously mentioned, other porous support materials such as titania and zirconia can also be used. In an embodiment, the present solid acid catalyst consists essentially of porous silica support (a mineral base) and the layer of sulfonated carbon. In an embodiment, the support containing porous silica may additionally include other support materials known in the art.

While, in general, a variety of porous silicas may be used for the support, in certain embodiments, silicas with relatively large pores are preferred. In certain embodiments, water-resistant silica is used.

It is noted that the sulfonated carbon layer disposed within the porous silica network, does not occupy the entire volume of the silica pores, but typically occupies a relatively small portion of the pores, such that the relatively large pores (voids) remain in the catalyst. Therefore, predominant pore size at maximum distribution (PPS) value in the catalyst is, in some cases, very similar, or is only insignificantly smaller than the PPS of the silica support used for catalyst preparation. For example, the catalyst having PPS of about 400 Å can be prepared using porous silica support with a PPS of about 450 Å. In some cases the difference in PPS between the present catalyst and the silica support that is used to prepare the catalyst is very small, e.g., less than 20%, or less than 10% of the PPS of silica support.

In certain embodiments, the PPS of the present catalyst is at least about 300 Å, for example, at least about 350 Å, or at least about 400 Å. For example, catalysts having PPS of about 300-600 Å, e.g., 400-550 Å are provided.

Depending on the pattern of pore size distribution, the average pore size (APS) of the present catalyst may vary. For example, a catalyst with APS of about 200 Å can have PPS of about 400 Å or 500 Å. In certain embodiments, APS of the present catalyst is in the range of 150-450 Å, e.g., 200-400 Å. Notably, the APS of the present catalyst may be higher than the APS of a silica support that is used for the catalyst preparation, presumably because very small pores may be blocked by the layer of sulfonated carbon, thereby increasing the relative proportion of larger pores in the catalyst.

The present solid acid catalyst is further characterized in certain embodiments by a large surface area, with BET parameter being at least about 50 m$^2$/g, such as at least 100 m$^2$/g. For example, catalysts with BET in the range of 50-250 m$^2$/g, such as 100-200 m$^2$/g are provided.

In certain embodiments, the present solid acid catalyst is characterized by a very high concentration of acidic —SO$_3$H sites. In certain embodiments, the concentration of —SO$_3$H groups is at least about 0.5 mmol/g and greater, often at least about 0.7 mmol/g and greater, such as at least about 1 mmol/g and greater. For example, in certain embodiments, catalysts with —SO$_3$H concentration of between about 0.5-1.5 mmol/g, such as between about 0.7-1.3 mmol/g are provided.

The present solid acid catalyst compares favorably with a number of conventional solid acids, due to its high H$^+$ concentration, high activity, good thermal stability, and mechanical robustness.

Thus, for example, the present catalyst can have a significantly higher H$^+$ concentration than traditional resin-based SAC-13 catalyst. The activities of the present catalyst, in certain embodiments, are significantly greater than activities of SAC-13, particularly at high temperatures (e.g., at temperatures of 120° C. and above).

In an embodiment, the present solid acid catalyst can exhibit very high activity in esterification reactions, especially in esterification of fatty acids.

In an embodiment, in addition to high activity the present solid acid catalyst is also characterized by low swelling, and good thermal stability. For example, in certain embodiments, swelling (volume increase) of the present solid acid catalyst upon exposure to a liquid esterification reaction mixture at 80° C. for 12 hours is less than about 20%, in some cases less than about 10%, such as less than about 5%. A liquid esterification mixture is understood to include a carboxylic acid (e.g., a fatty acid), an alcohol, and, optionally, ester and water.

The present catalysts can be prepared in a variety of forms including fixed catalyst beds, granules, powders, etc. The beds can be fixed in the reactors, or packed catalyst columns may be used. The catalysts can be employed in a variety of reactors, such as fixed bed batch reactors, fixed bed continuous flow reactors, and slurry reactors.

The present solid acid catalysts can be used in a variety of acid-catalyzed reactions described in the literature. For example, the present catalysts can be used in the reactions which are known to be catalyzed by SAC-13, WO$_3$/ZrO$_2$, sulfonated zirconia and other solid acid catalysts. The conditions for performing acid-catalyzed reactions with the present catalysts can be similar to conditions employed for other solid acid catalysts.

For example, a variety of reactions catalyzed by SAC-13, which can also be catalyzed by the present solid acid catalyst under similar conditions, are described in the article titled "Nafion-Silica Nanocomposites: A New Generation of Water-Tolerant Solid Acids of High Efficiency" by A. Molnar published in *Current Organic Chemistry*, 2008, 12, 159-181, which is incorporated herein by reference. Such reactions include Friedel-Crafts and related reactions (e.g., Friedel-Crafts alkylation and acylation), various transformations of alkenes (e.g., isomerization, dimerization, alkane-alkene alkylation, and additions), various transformations of alcohols (e.g., direct esterification, dehydration, the Ritter reaction), protective group chemistry, chemistry of heterocycles, oxidations, and other reactions.

Notably, due to high activity of the present solid acid catalysts, in certain embodiments, the acid-catalyzed reactions can be performed at lower temperatures than employed for less active conventional catalysts, such as SAC-13. For example, some catalytic reactions which were previously described as being catalyzed at temperatures of greater than 90° C., can be performed using the present solid acid catalysts at lower temperatures, e.g., at 60-80° C. At the same time, due to high thermal stability of the present solid acid catalyst, it also allows performing catalytic reactions at high temperatures, e.g., at temperatures of about 130-250° C., e.g., of about 150°-200° C. These temperatures were previously inaccessible for use with many conventional resin-based catalysts, due to decomposition and loss of activity that occurs in many acid resins at temperatures of greater than about 125° C.

Accordingly, due to high activity and good thermal stability the present solid acid catalysts can be used in acid-catalyzed reactions at a larger temperature range than was possible with conventional resin-based catalysts. In certain embodiments, this property is exploited by performing acid-catalyzed reactions using a temperature gradient. In these embodiments, the acid-catalyzed reaction is started at a lower temperature, and, as the activity of the catalyst decreases during the course of the reaction, the temperature is increased gradually or in a step-wise fashion to a higher temperature, in order to preserve sufficient reaction rate. Usually the temperatures from a range of 60-250° C. are used. In certain embodiments, the reaction is started at a temperature that is lower than 90° and is conducted with an accompanying temperature increase to a temperature that is higher than 130° C.

Such a range of operational temperature ranges were previously inaccessible with many conventional solid acid catalysts.

Methods of Making the Present Solid Acid Catalysts

The present solid acid catalyst can be prepared, in an embodiment, by following the process flow sequence shown in FIG. 1. As shown in 101, the process starts by impregnating a porous silica support with a phenol-containing material. A variety of porous silicas (including commercially available silicas) can be used. In certain embodiments, silicas with relatively large pore size are preferred. For example, in certain embodiments silica supports are characterized by APS of at least about 100 Å, at least about 150 Å, or at least about 200 Å, and have PPS of at least about 400 Å, at least about 450 Å, such as at least about 500 Å. In certain embodiments silicas are characterized by APS in the range of about 150-250 Å, and PPS in the range of about 400-550 Å. Further, silicas with relatively large surface area, such as with BET parameter of at least about 100 m$^2$/g, or at least 150 m$^2$/g are used in certain embodiments. In certain embodiments water resistant silicas are used. Examples of commercially available silicas that are suitable for catalyst preparation include without limitation Water Resistant Silica Gel (available from SilicaStar Industries, Fremont, Calif.) and MA 1620 silica (available from PQ corporation).

Impregnation of silicas with a phenol-containing material generally can be carried out using a number of methods, including incipient wetness, co-deposition, co-precipitation, etc. In certain embodiments pre-formed silicas (such as commercially available silicas described above) are contacted with a phenol-containing material (e.g., in solution), such that the phenol-containing material is allowed to mix with silica and to diffuse into the porous silica network.

After silica is impregnated with the phenol-containing material, the material is processed in operation 103 to form a polymer within the pores of the porous silica support. Depending on the nature of the phenol-containing material, such processing can take a number forms. In certain embodiments, it is preferred that such processing results in formation of a cross-linked polymer. For example, silica may be impregnated with a cross-linkable polymer, oligomer, or a low-molecular weight phenol-containing material, which is subsequently cross-linked in operation 103 via curing operation. Curing can be performed, for example, chemically (e.g., by contacting the phenol-containing material with a curing agent), thermally (e.g., by heating the material), or by treating the material with electromagnetic radiation (e.g., exposing to UV or other type of radiation). In certain embodiments, silica is impregnated with phenol-formaldehyde epoxy resins (typically oligomers or low molecular weight polymers), which are cured chemically or thermally.

In certain embodiments, silica may be impregnated in operation 101 with phenol-containing monomers, and processing of monomers in operation 103 can include polymerization which may be optionally accompanied by cross-linking and curing.

In yet other embodiments, silica may be impregnated in operation 101 with a phenol-containing polymer (e.g., a polymer applied in solution) and processing may simply include allowing the polymer to diffuse into the porous network for a period of time, allowing the solvent to evaporate (with or without heating), or curing the structure to form a cross-linked polymer.

Generally, processing operation 103, may be performed after the impregnation operation 101, or these operations can partially or completely overlap in time.

In one implementation of the process, a phenol-formaldehyde epoxy resin is mixed with a solvent (e.g. ethyl acetate), and a curing agent (e.g., 2-ethyl-4-methylimidazole) is added to the solution and is followed by addition of silica. The materials are thoroughly mixed and are left for a period of time to allow for impregnation and curing. Alternatively, instead of addition of the curing agent, the mixture can be cured by heating, or by exposure to electromagnetic radiation (e.g., UV exposure). Examples of suitable phenol-formaldehyde epoxy resins include without limitation novolac epoxy resins, such as DEN 438-A85 (available from Dow Chemical), epoxy resins containing bisphenol A, such as EPALLOY 7190-A83 (available from Emerald Performance Materials), and mixtures thereof.

As a result of impregnation 101, and processing 103, a porous silica support having a polymer containing aromatic groups disposed within the porous silica network is obtained. Next, the polymer is carbonized in operation 105, by exposing the structure to high temperature in a non-oxidizing atmosphere, such that a carbon layer is formed within the porous silica network. Carbonization is performed in a non-oxidizing atmosphere in order to avoid burning of the polymer. For example, the structure may be heated in an inert gas atmosphere, such as an atmosphere including $N_2$, He, Ar, Ne, Kr, or mixtures thereof. In certain embodiments carbonization is performed by heating the partially formed catalyst at a temperature of at least about 200° C. for at least one hour. In one specific implementation, carbonization is performed by heating the partially formed catalyst at a temperature of about 120° C. for two hours followed by heating at 400° C. for four hours. It is understood, that carbonization does not necessarily have to be complete, and stripping of all hydrogen atoms from the polymer is not required. Therefore, the formed carbon layer, which is also sometimes referred to as "coke", may contain H atoms and other elements in addition to carbon. In certain embodiments, only partial carbonization is preferred, and the structure is not heated at temperatures exceeding 600° C.

Next, in operation 107 the partially prepared catalyst is treated with a sulfonating agent to form a sulfonated carbon layer within the porous silica support. In one implementation the carbon layer is sulfonated by contacting the partially prepared catalyst with sulfuric acid, often with heating. For example, sulfonation can be carried out by treating the structure with 96% $H_2SO_4$ at about 150° C. for a period of four hours.

Certain embodiments can include removing excess sulfate ions remaining in the partially formed catalyst structure after sulfonation. This can be performed, as illustrated in operation 109, by simply washing the catalyst. For example the catalyst can be washed with deionized water until no sulfate ions are detectable in the washes.

Next, in operation 111, the formed structure is dried, e.g., by heating under vacuum, to provide the present solid acid catalyst.

It is understood that other porous supports with sufficient porosities, such as titania and zirconia can be similarly impregnated with phenol-containing materials and processed to form a solid acid catalyst including sulfonated carbon layer within the porous network of the support. Suitable supports are selected such that they do not significantly react with sulfuric acid during the sulfonation step.

A number of acid-catalyzed reactions that can be catalyzed by the present solid acid catalysts will be described as illustrations. It is understood that the list of reactions is illustrative and not exhaustive, and that the present solid acid catalysts can be used in a variety of other reactions that are known to be acid-catalyzed.

Alkylation Reaction

The present solid acid catalyst can be used in a number of alkylation reactions, including alkane/alkene alkylation and Friedel-Crafts alkylations of aromatic substrates with alkyl halides (e.g., alkyl chlorides, alkyl bromides or alkyl iodides) or olefins. The method of performing alkylation includes providing a mixture including an alkylation substrate (e.g., an alkane or an aromatic compound) and an alkylating agent (e.g., an olefin, or an alkyl halide) and contacting the mixture with the present solid acid catalyst. The reaction is allowed to proceed under suitable conditions for a period of time, and the alkylated product is later collected. The reaction can proceed in a batch reactor or in a continuous flow reactor. The reaction mixture can be passed over or through a fixed catalyst bed. In certain embodiments a slurry of the catalyst in the reaction mixture can be used.

In some implementations, the reaction mixture includes neat starting materials (without a solvent). In other embodiments, co-solvents are used, including traditional organic solvents, as well as supercritical solvents, and near-supercritical solvents, such as supercritical $CO_2$.

Alkane/Alkene Alkylation

Alkane/alkene alkylation is an industrially significant reaction in which a saturated substrate (alkane) is alkylated by an alkene in a presence of a catalyst. The alkylation of isobutane with light olefins ($C_3$-$C_5$) is a refinery process used to produce alkylates, which are useful components of gasoline. Trimethylpentanes (TMPs) are highly desired compounds among the alkylates due to their high octane numbers. An example isobutene/but-2-ene alkylation is illustrated by Equation (1):

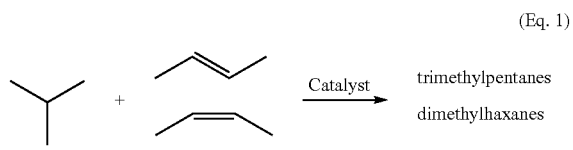

(Eq. 1)

Conventionally, in industrial implementation this reaction is catalyzed by sulfuric or hydrofluoric acid. Due to corrosive and toxic nature of these substances, a significant effort has been spent in searching for an environmentally benign solid acid catalyst replacement.

Figure 2:
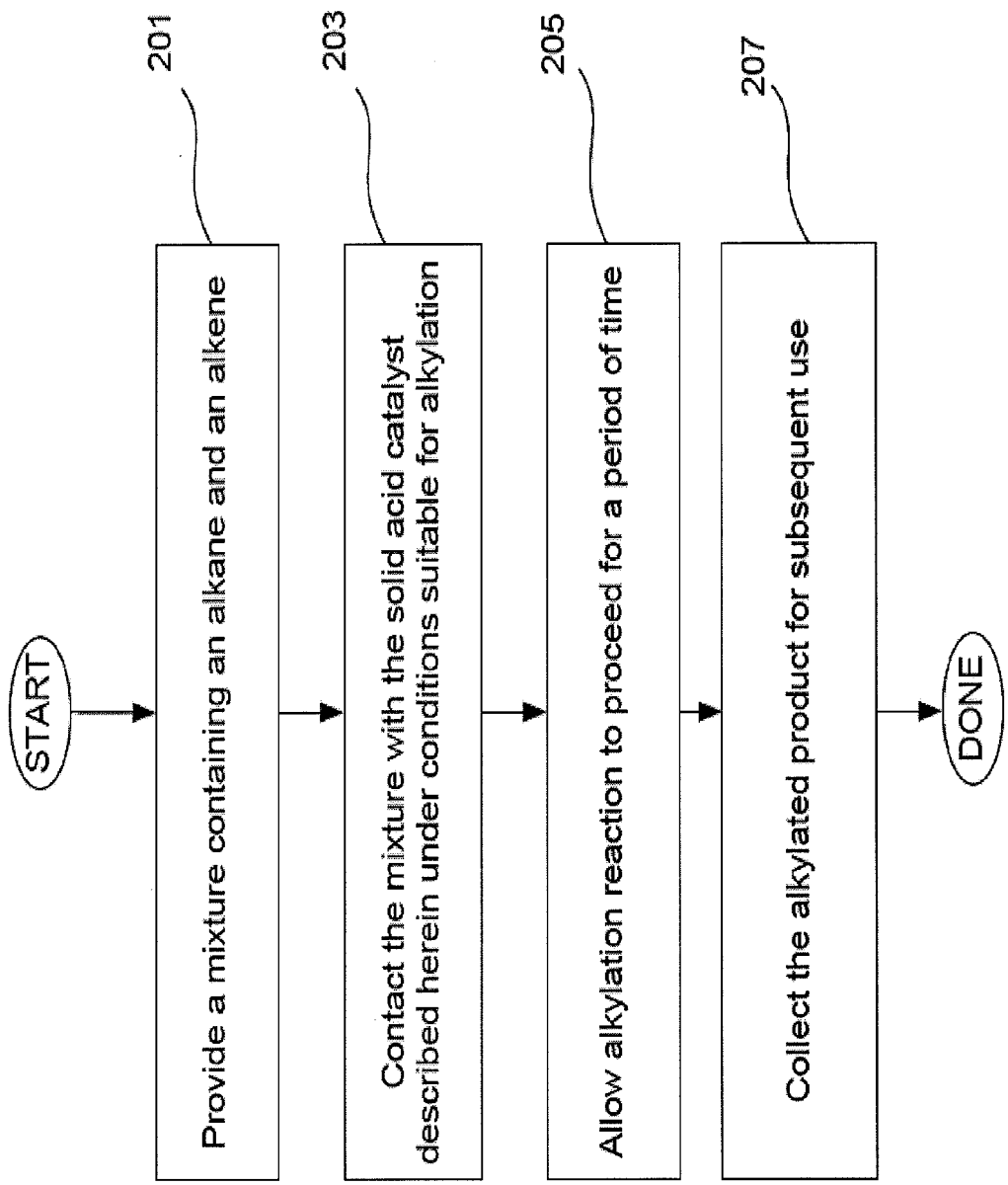
FIG. 2 is an exemplary process flow diagram for a method of performing alkylation using the present solid acid catalyst.

In an embodiment of the present invention, the present solid acid catalyst is used to catalyze alkane/alkene alkylation. Referring to a process flow diagram shown in FIG. 2, the process is implemented by providing a mixture containing an alkane and an alkene as shown in 201; contacting the mixture with the present solid acid catalyst under conditions suitable for alkylation in 203; allowing the alkylation reaction proceed for a period of time in 205; and collecting the alkylated product for subsequent use in 207.

In certain embodiments the starting material includes or consists essentially of a mixture of isobutene and a butene (but-2-ene, but-1-ene or mixtures thereof). For example, in certain embodiments the starting material is a C-4 cut refinery product, which contains n-butane, isobutene, n-butenes, and, optionally, isobutenes. The reaction can proceed under conditions that are similar to or are identical to conditions described for alkane/alkene alkylation with other solid acid catalysts. For example, applicable conditions, applicable starting materials (e.g., Raffinate II composition) and an applicable reactor design (e.g., batch reactor) are described in an article titled "Alkylation of Raffinate II and Isobutane on Nafion Silica Nanocomposite for the Production of Isooctane" by Kumar et al. (*Energy & Fuels* 2006, 20, 481-487), which is incorporated herein by reference.

In one specific implementation, isobutane/butene alkylation proceeds without a co-solvent in a temperature range of between about 60° C.-100° C., with at least about 10-fold molar excess of isobutane over butenes as starting materials. Further, because, in certain embodiments, the present solid acid catalyst can be more thermally stable than nafion silica nanocomposites described by Kumar et al., the alkane/alkene alkylation with the present solid acid catalyst can be also accomplished at higher temperatures, e.g., at temperatures greater than 100° C., such as greater than 130° C.

Another example of applicable conditions is described, for example in an article by Sarsani et al., titled "Isobutane/butene Alkylation on Microporous and Mesoporous Solid Acid Catalysts: Probing the Pore Transport Effects with Liquid and Near Critical Reaction Media" (*Green Chem.*, 2009, 11, 102-108), which is incorporated herein by reference. For example, the reaction may be carried out in critical or near critical $CO_2$ or in dense ethane as diluent.

Further, another set of appropriate conditions and reactor designs for use with the present solid acid catalyst is described in the U.S. Pat. No. 6,924,407 by Subramaniam et al, issued Aug. 2, 2005, which is incorporated herein by reference.

The conditions for alkane/alkene alkylation described above are not limiting and are shown for illustration purposes.

After the alkylation reaction is allowed to proceed for a period of time the resulting alkylates (e.g., isooctanes) are collected for subsequent use as gasoline components.

Friedel-Crafts Alkylation

Another alkylation reaction catalyzed by the present solid acid catalyst is Friedel-Crafts alkylation of aromatic substrates. In one embodiment alkylation is accomplished by contacting the catalyst with a mixture of an aromatic compound (e.g., a substituted or substituted benzene or naphthalene) and an alkene (e.g., 1-alkene), to effect alkylation of the aromatic substrate. The resulting alkylated substrate is subsequently collected from the reaction mixture. Friedel-Crafts reactions that can be catalyzed by the present solid acid catalyst are described in *Current Organic Chemistry*, 2008, 12, 159-181, at pages 163-166 (which has been incorporated herein by reference).

Among Friedel-Crafts alkylation reactions, of particular interest are alkylations of benzene with 1-alkenes to form linear alkylbenzenes, which play an useful role in industrial production of surfactants. The alkylation reaction includes, in one embodiment, contacting a mixture including benzene and a $C_9$-$C_{16}$ linear 1-alkene with the present solid acid catalyst to effect alkylation. The reaction is allowed to proceed for a period of time, and the product is subsequently collected.

In certain embodiments, reaction conditions and reactor designs that can be used with the present solid acid catalysts are described in US Patent Publication 2004/0260133 titled "Process for the Production of Phenylalkanes in the Presence of a Solid Acid Catalyst the Deactivation of Which is Delayed", by Guillon et al. published Dec. 23, 2004, which is incorporated herein by reference.

In an embodiment, Friedel-Crafts alkylation is performed by contacting a mixture of an aromatic substrate and an alkyl halide (e.g., chloride, bromide, or iodide) with the present solid acid catalyst to effect alkylation of an aromatic substrate. Further, in certain embodiments, the present solid acid catalyst is used for alkylation of aromatics with an alcohol, e.g., with a benzyl alcohol, such as described in *Current Organic Chemistry*, 2008, 12, 159-181, at page 164 (which has been incorporated herein by reference).

Disproportionation of Alkylaromatics and Transalkylation

The present solid acid catalysts can also be used to catalyze disproportionation of alkylaromatic substrates. The reaction includes contacting an alkyl-substituted aromatic compound with a solid acid catalyst to produce a disproportionation product, for example as shown by a forward reaction in Equation (2):

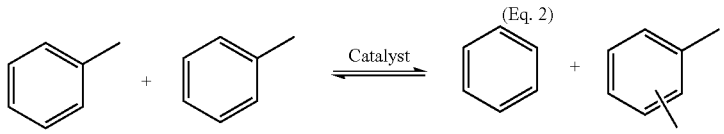

(Eq. 2)

The present solid acid catalyst can also be used to catalyze the reverse reaction shown in Equation (2), when conditions are appropriately adjusted to shift the reaction equilibrium to the left (e.g., by removing the reaction products). The reverse reaction is referred to as transalkylation.

Friedel-Crafts Acylation

The present solid acid catalyst can also catalyze acylation of aromatic substrates, such as those described in *Current Organic Chemistry*, 2008, 12, 159-181, at pages 166-167 (which has been incorporated herein by reference).

Figure 3:
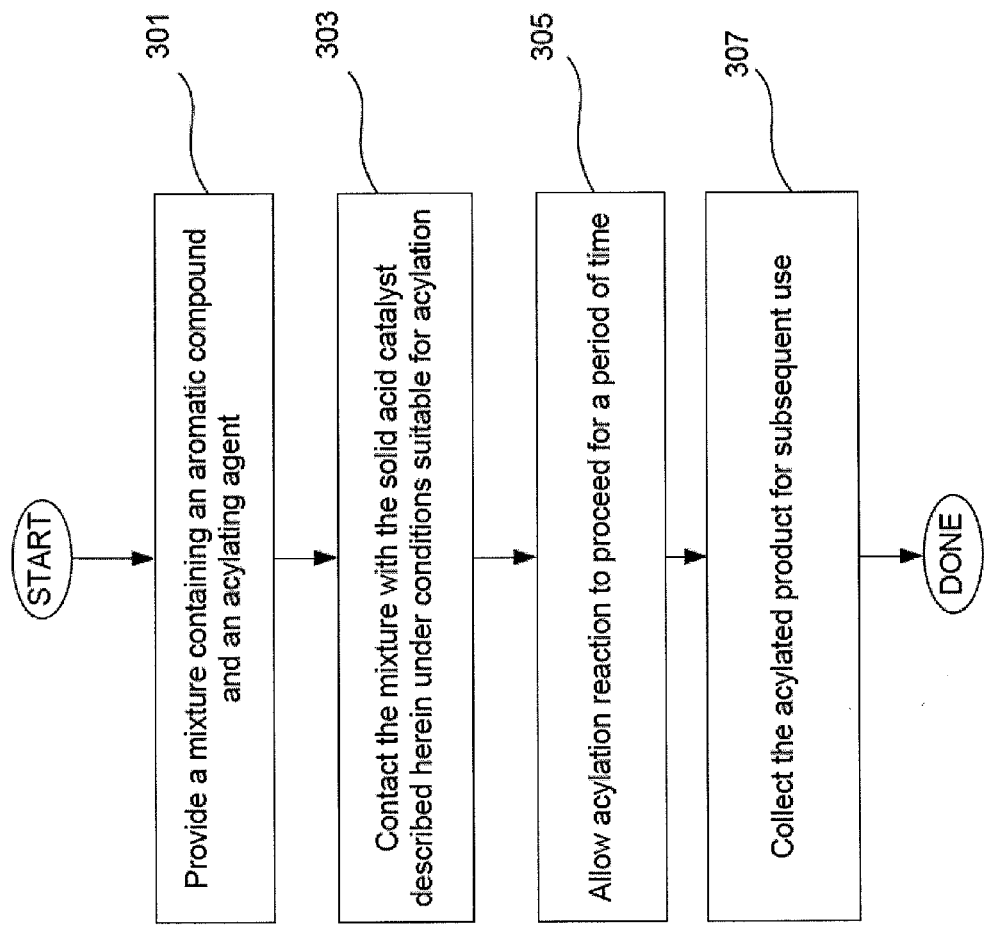
FIG. 3 is an exemplary process flow diagram for a method of performing acylation using the present solid acid catalyst.

Referring to FIG. 3, a process flow diagram for a Friedel-Crafts acylation is shown. The process starts by providing a mixture containing an aromatic compound and an acylating agent in 301. A variety of aromatic compounds including but not limited to substituted or unsubstituted benzene, and substituted or unsubstituted naphthalene, may be acylated. The acylating agents include without limitation acyl halides, acid anhydrides, carboxylic acids, and carboxylic acid esters. In certain embodiments, the acylation is intramolecular, that is, the starting material molecule includes both the aromatic moiety and the acylating moiety, and the acylation proceeds intramolecularly with a formation of a cycle, fused to the aromatic rings.

Referring again to FIG. 3, in operation 303, the reaction mixture is contacted with the present porous solid acid catalyst, and the reaction is allowed to proceed for a period of time in operation 305. Next, in 307, the acylated product is collected for subsequent use.

In one specific non-limiting example, reaction conditions and starting materials, described in an article titled "Nafion/Silica Composite Material Reveals High Catalytic Potential in Acylation Reactions" by Heidekum et al. (*Journal of Catalysis*, 1999, 188, 230-232), are used with the present solid acid catalyst. This article is incorporated herein by reference.

Further, in other embodiments, the provided catalyst is used in acylation reactions under reaction conditions that are similar to those described in US Patent Application Publication 2005/0222457 by Okuhara et al., published Oct. 6, 2005, which is herein incorporated by reference.

Etherification Reaction

In an embodiment, the present solid acid catalyst is used in an etherification reaction.

In one aspect, the etherification reaction is a reaction between an alkene and an alcohol which results in formation of an ether. An illustration of such reaction, where an alkene is a C6-alkene and the alcohol is methanol, is shown in Scheme 14, in *Current Organic Chemistry*, 2008, 12, 159-181, at page 170 (which has been incorporated herein by reference). In general, a wide variety of alkenes (e.g., C2-C12 alkenes), and different alcohols, including but not limited to methanol, ethanol, propanol, and butanol (including their isomers) may be used. A variety of valuable gasoline oxygenate additives, including methyl t-butyl ether (MTBE), and heavier C5 and C6 ethers can be prepared in this fashion.

In another aspect, the etherification reaction is a reaction between two alcohols resulting in formation of an ether. The alcohols may be the same or different, and may include without limitation methanol, ethanol, propanol, and butanol (including their isomers). In an embodiment, the present solid acid catalyst is used in a reaction of forming dibutyl ethers from aqueous 2-butanol. The reaction conditions can be those described in US Patent Application Publication No. 2008/0132733 by Manzer et al., published Jun. 5, 2008, which is incorporated herein by reference. In an embodiment, the present solid acid catalyst is used for formation of dimethyl ether from methanol. The conditions for this reaction can be those described by Jun et al., in US Patent Application Publication No. 2006/0135823, which is incorporated herein by reference. In an embodiment, the present catalyst has a good thermal stability and can be used at temperatures of greater than about 100° C., for example, for etherification.

Figure 4:
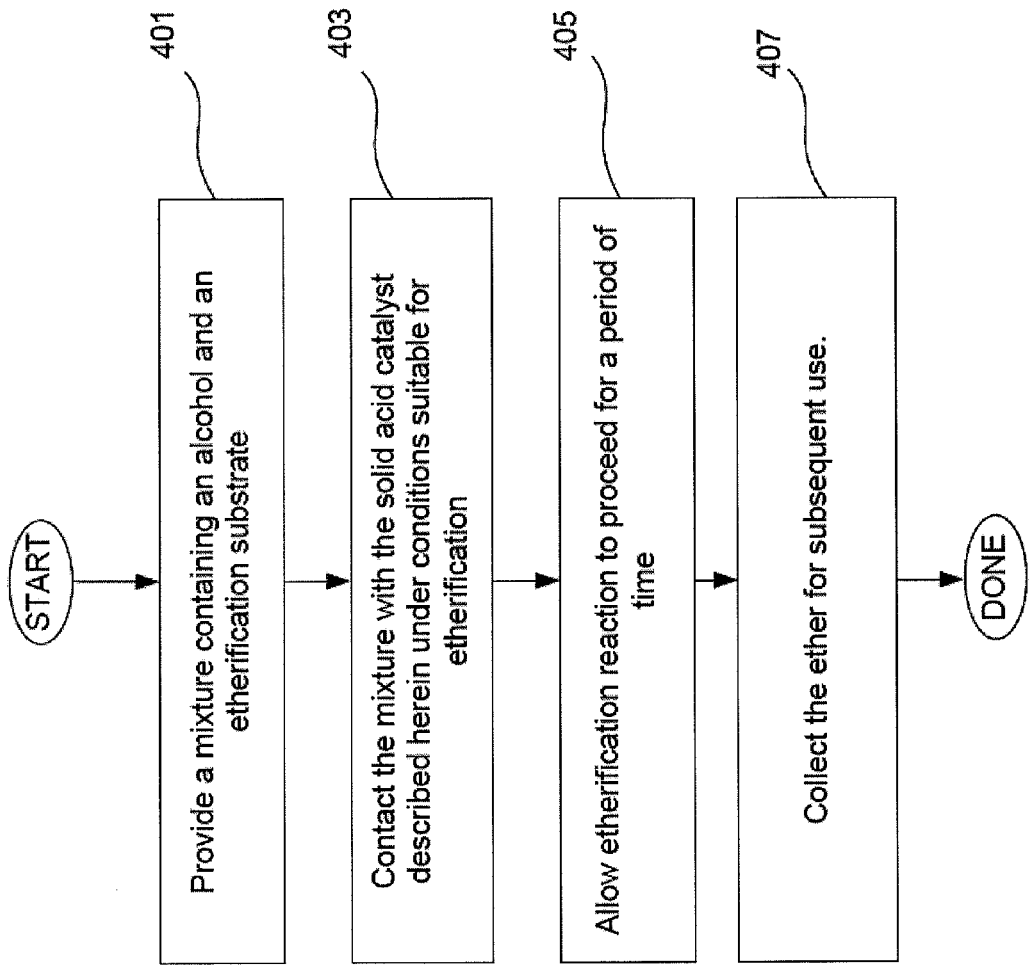
FIG. 4 is an exemplary process flow diagram for a method of performing etherification using the present solid acid catalyst.

Referring to FIG. 4, a process flow diagram for an etherification reaction is shown. The process starts in 401 by providing a mixture containing an alcohol and an etherification substrate. As described above, depending on the type of etherification, the substrate may include an alkene or an alcohol. In operation 403, the mixture is contacted with the present solid acid catalyst under conditions suitable for etherification. The etherification reaction is allowed to proceed for a period of time as shown in operation 405. The formed ether is then collected for subsequent use in 407.

Hydration of Olefins

Hydration of olefins to form corresponding alcohols as well as the reverse reaction of alcohol dehydration which results in formation of the olefins are two acid-catalyzed processes which can be implemented with the use of the present solid acid catalyst.

An example of these reactions is shown in Equation 3, which shows isopropanol formation upon hydration of propene, as well as the reverse isopropanol dehydration reaction. The present solid acid catalyst can be used in this reaction.

Although not limiting to the present invention, it is believed that this usefulness may be due to the high acid strength of the present solid acid catalyst, its high thermal stability, its low swelling (e.g., as compared to Amberlyst resin beads), or a combination thereof.

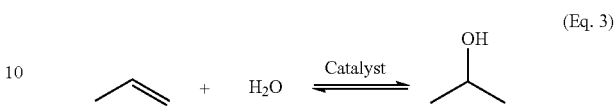

(Eq. 3)

Figure 5:
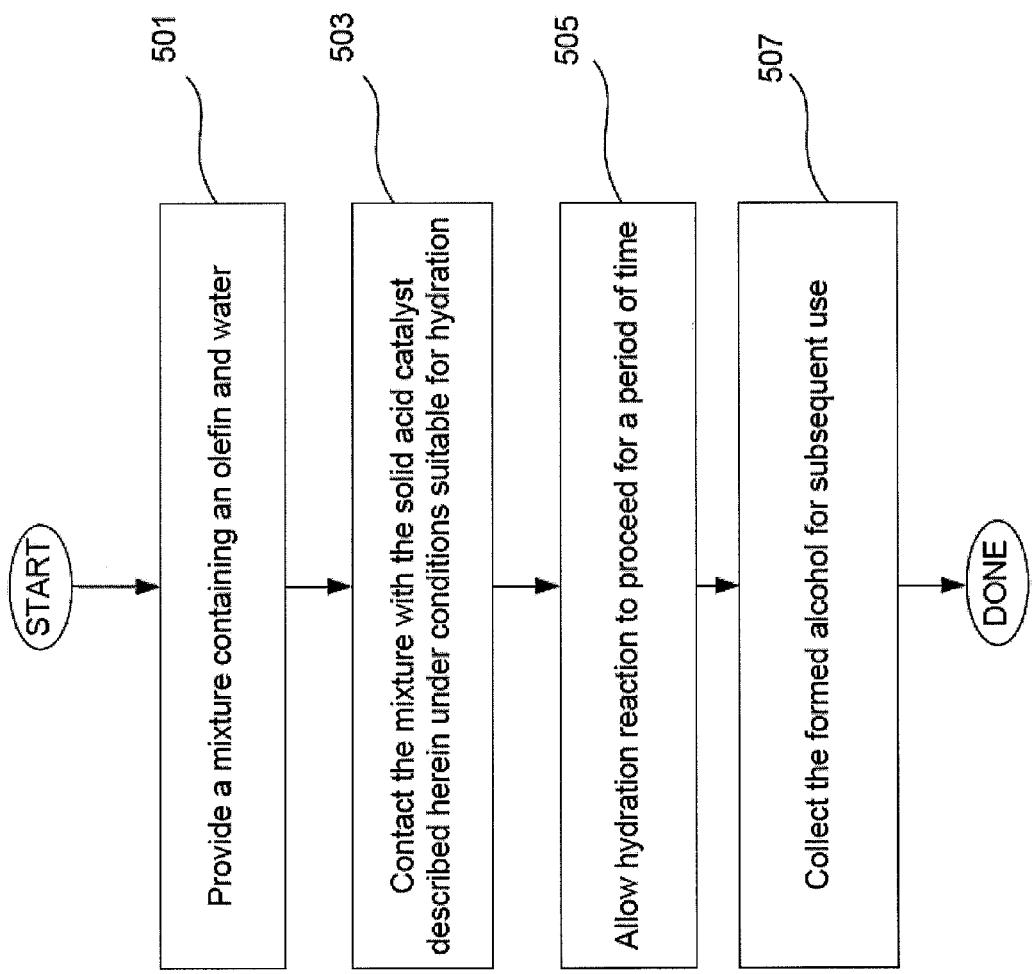
FIG. 5 is an exemplary process flow diagram for a method of performing olefin hydration using the present solid acid catalyst.

The process flow diagram for olefin hydration reaction is shown in FIG. 5, where the process starts in 501 by providing a mixture containing an olefin (e.g., ethane, propene, a butene, a pentene, etc) and water. The mixture may be liquid or in a gaseous phase. The mixture contacts the present solid acid catalyst under conditions that are suitable for hydration (e.g., large excess of water, and temperature ranging from 60° C. to 200° C., such as from 130° C. to 200° C.), as shown in operation 505. The reaction is allowed to proceed for a period of time as shown in 505, after which time the formed alcohol is collected for subsequent use in operation 507

The reverse reaction (alcohol dehydration) can also be accomplished using the present solid acid catalyst, when the conditions are adjusted such that the equilibrium is shifted to the left (e.g., by water removal). The reaction is accomplished by contacting the present solid acid catalyst with an alcohol under suitable reaction conditions, such as described in *Current Organic Chemistry*, 2008, 12, 159-181, at pages 172-173 (which has been incorporated herein by reference). Further, in one example, the present solid acid catalyst can be used in alcohol dehydration (e.g., for formation of a butene from butanol) using conditions described in the US Patent Application Publication No. 2008/0132732, which is incorporated herein by reference.

Olefin Double Bond Isomerization

In certain embodiments, the present solid acid catalyst is used to catalyze isomerization of an olefin, effecting double bond migration. An example isomerization reaction is isomerization of but-1-ene to but-2-ene(s). These double bond migration reactions can be performed even under relatively mild conditions, e.g., at temperatures less than about 100° C., e.g., at less than about 70° C.

Figure 6:
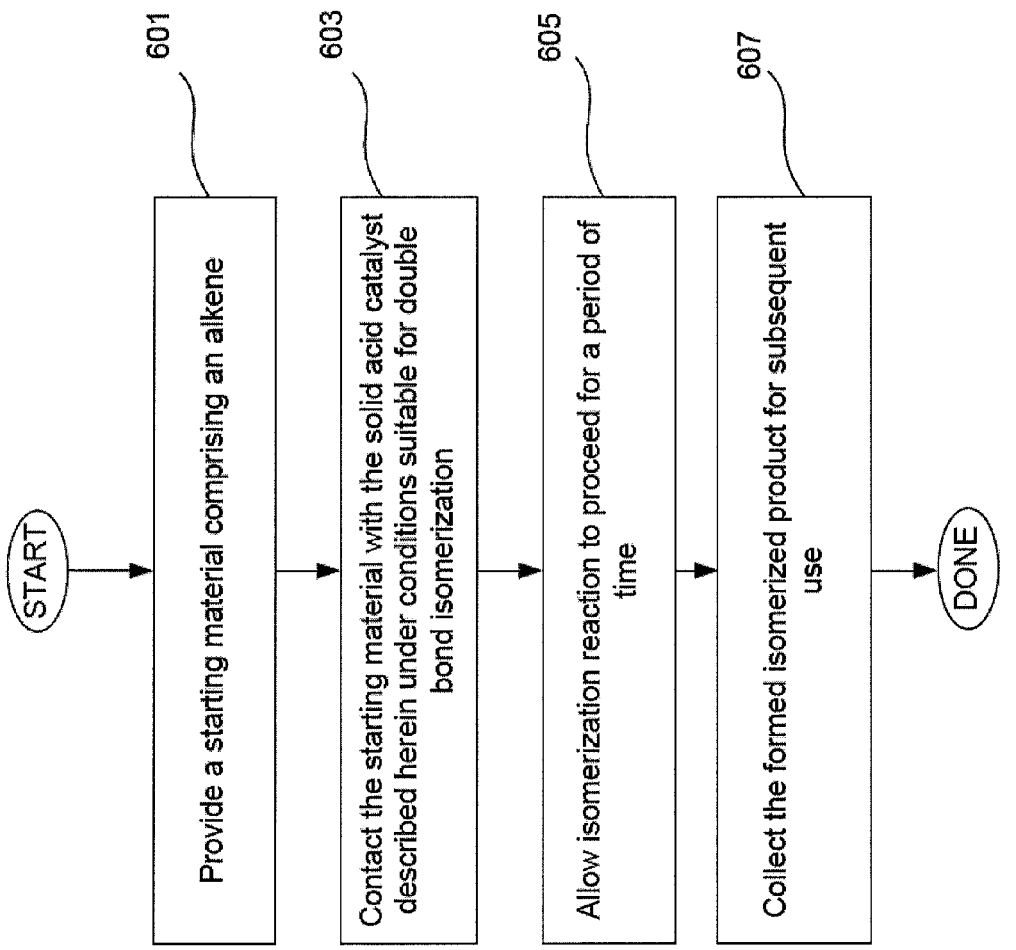
FIG. 6 is an exemplary process flow diagram for a method of performing isomerization using the present solid acid catalyst.

Referring to a process-flow diagram shown in FIG. 6, the process starts by providing an alkene in operation 601. Typically, a terminal alk-1-ene is provided, such but-1-ene, pent-1-ene, hex-1-ene, etc.). The alkene contacts the present solid acid catalyst in operation 603 under conditions suitable for double bond isomerization (i.e., migration). The reaction is allowed to proceed for a period of time, as shown in 605, and the resulting isomerized product is collected for subsequent use.

Esterification Reaction

In an embodiment, the present solid acid catalyst can be used to catalyze an esterification reaction. In certain embodiments, the present solid acid catalyst can be highly active esterification catalysts with activities exceeding those of conventional SAC-13 catalyst by at least two-, three-, or even ten-fold. For example, the present solid acid catalyst can be at least two or three times more active than SAC-13 in esterification of lauric acid with methanol at 80° C., and can be more than ten times more active than SAC-13 when the same reaction esterification reaction is performed at 120° C. In certain embodiments, the present solid acid catalyst shows activities of at least 150 mL/hours·g for esterification of lauric acid with excess methanol performed at 80° C.

In addition, embodiments of the present solid catalyst can have higher thermal stability than SAC-13. In certain embodiments, the present solid acid catalyst retains at least 30% of its initial activity (measured as activity for an esterification reaction of lauric acid with methanol at 80° C.) upon exposure to an esterification reaction mixture at 120° C. for 12 hours.

Figure 7:
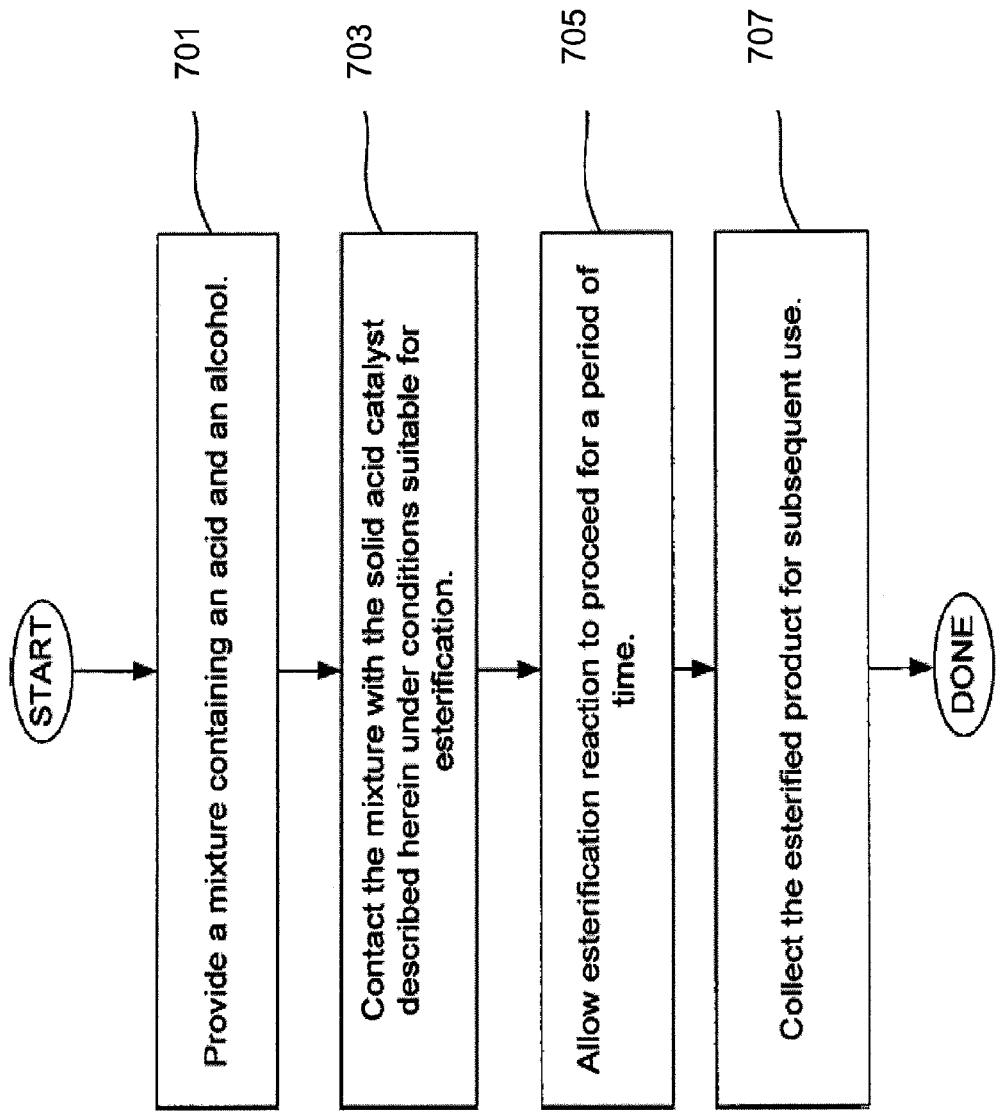
FIG. 7 is an exemplary process flow diagram for a method of performing esterification using the present solid acid catalyst.

An process flow diagram for an embodiment of a method of performing the present catalyzed esterification reaction is shown in FIG. 7. The process starts in 701 by providing an esterification reaction mixture containing an acid and an alcohol. In general, the present solid acid catalyst can be used in conjunction with a number of low- and high-molecular weight acids and alcohols. Examples of acids include but are not limited to formic, acetic, propionic, butyric, valeric, caprylic, lauric, stearic, palmitic, linoleic, linolenic, oleic acids and various mixtures thereof. Examples of alcohols include but are not limited to methanol, ethanol, propanol, isopropanol, butanol, ethylene glycol, glycerin and their various mixtures. In an embodiment, the present catalyst is used for esterification of fatty acids with lower monohydric alcohols, such as methanol and ethanol.

The mixtures, containing an acid and an alcohol may contain additional components. For example, in certain embodiments, in addition to an acid and an alcohol, the mixtures further contain triglycerides and, optionally, water. The mixtures may be essentially solvent-free, or, in other embodiments, a suitable co-solvent, such as tetrahydrofuran may be added. In certain embodiments, the initial esterification reaction mixture containing triglycerides is primed by addition of fatty acid esters (e.g., methyl or ethyl esters) to improve miscibility of triglycerides with the alcohol.

In one implementation, the mixture includes or consists essentially of a fat or oil of vegetable or animal origin, having FFA content of at least about 0.3% wt., such as at least 0.5% wt., or at least 5% wt. and a monohydric alcohol, such as methanol, ethanol, propanol or butanol. In an embodiment, the monohydric alcohol is or includes methanol.

In operation 703, the mixture is contacted with the present solid acid catalyst under conditions suitable for esterification. Esterification reaction can be performed at a wide temperature range, for example, at between about 70° C. and about 250° C., more typically between about 80° C. to about 200° C. at atmospheric pressure or in high pressure reactors at a pressure range of about 1-20 atm. The choice of particular temperatures and pressures will depend on the nature of starting materials, and, specifically, on the nature of alcohol used for esterification. When methanol is used, the temperatures are usually in the range of 80° C. and 200° C., and the pressures are higher than one atmosphere, e.g., between about 2-10 atm. In an embodiment, with the use of the present catalyst, relatively low temperatures of about 80° C. and pressures of about 2 atmospheres can be used in the present esterification reaction.

In an embodiment, the present catalyst can operate at high temperatures without substantial degradation. Thus, for example, while conventional acid resin-based catalysts often mechanically degrade and lose activity at temperatures greater than 120° C., the present catalyst can remain active at about 120 to about 200° C., such as about 150° C. to about 200° C. In certain embodiments, the method includes conducting the esterification reaction using temperature gradient. For example, the catalytic esterification in one embodiment is started at low temperature (e.g., 80° C.) and the temperature is increased during the course of the reaction in order to maintain sufficient reaction rates. In an embodiment, with the use of the present solid acid catalyst, the temperature can be increased to 150° C. and even 200° C., which was previously not possible with the use of conventional thermally unstable resins.

In certain embodiments, the alcohol is used in excess with respect to the acid. For example, at least about 2-fold molar excess of alcohol can be used.

As shown in 705, the esterification reaction is allowed to proceed for a period of time (typically several hours), whereupon the esterified product is collected. In certain embodiments, it is desirable to remove water that is formed in the esterification reaction. In certain embodiments esterification is performed in several steps, with water being removed after each consecutive step. For example, esterification may proceed in a first reactor, then water is removed e.g., by distillation or evaporation (e.g., with reduced pressure, elevated temperature or both), and the resulting dried reaction mixture is directed to a second reactor to further esterification, whereupon water may be again removed, and the esterification may be further repeated. The esterification/water removal cycle can be repeated as many times as necessary. In certain embodiments between 2-4 esterification steps are sufficient. In other embodiments, water is removed from the esterification reaction mixture continuously during the course of the esterification reaction. Upon esterification, and optional water removal, the esterified product is collected for subsequent use as shown in operation 707. For example, methyl esters of fatty acids can be collected for use as biodiesel fuels. In certain embodiments, the mixtures containing esterified products and fatty acid triglycerides are collected and subjected to subsequent processing (e.g., transesterification). It is understood that, while the present catalyst is useful for FFA esterification in biodiesel feedstocks having high FFA content, the present catalyst can be employed to catalyze esterification of a variety of substrates in a wide range of applications.

Further, it is understood that, in an embodiment, the present solid acid catalyst can be used to catalyze hydrolysis, a reverse reaction to esterification. When hydrolysis is performed, a mixture containing an ester and water is contacted with the present solid acid catalyst under conditions that are suitable for hydrolysis (e.g., large excess of water and removal of hydrolysis reaction products) to obtain an acid and an alcohol.

Transesterification Reaction

In certain embodiments, the present catalyst is used to catalyze a transesterification reaction. Any of a variety of transesterifications can be catalyzed. In certain embodiments, the catalyst is used to catalyze transesterification of fatty acid triglycerides with monohydric alcohols, such as methanol, ethanol, propanol, and butanol. In an embodiment, methanol is used for transesterification.

Figure 8:
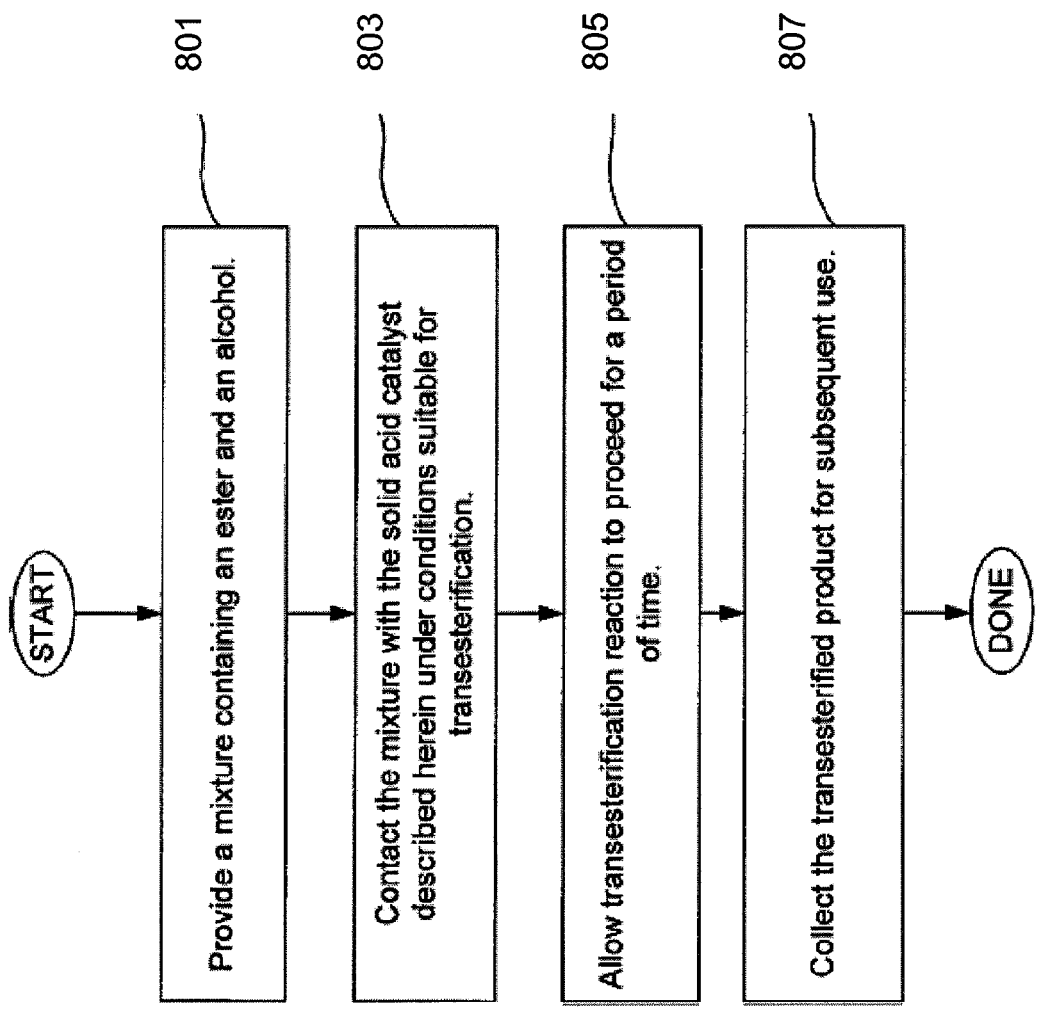
FIG. 8 is an exemplary process flow diagram for a method of performing transesterification using the present solid acid catalyst.

An process flow diagram for performing a transesterification reaction according to the present invention is shown in FIG. 8. The process starts in operation 801 by providing a mixture containing an ester and an alcohol, where the alcohol is different from the alcohol that is released from the ester upon transesterification. For example, a mixture containing fatty acid triglycerides and methanol may be provided, to form glycerin and fatty acid methyl esters. However, transesterification of a variety of esters beyond triglycerides can be similarly accomplished.

In operation 803, the mixture is contacted with the present solid acid catalyst, under conditions that are suitable for transesterification. In one implementation, catalytic transesterification is performed at a temperature of about 120-200° C. under pressure. As shown in operation 805, the transesterification reaction is allowed to proceed (typically for several hours), and, in 807, the transesterified product is collected for subsequent use (or processing). For example, a mixture of methyl esters of fatty acids and glycerin is collected for subsequent separation of glycerin and subsequent use of methyl esters in biodiesel fuels.

Processing of Biodiesel Feedstocks Using the Present Solid Acid Catalyst

Esterification and transesterification reactions catalyzed by the present solid acid catalyst can be integrated into process flows for biodiesel feedstock processing in a number of ways.

Using the Present Solid Acid Catalysts for FFA Pre-Esterification

Figure 9:
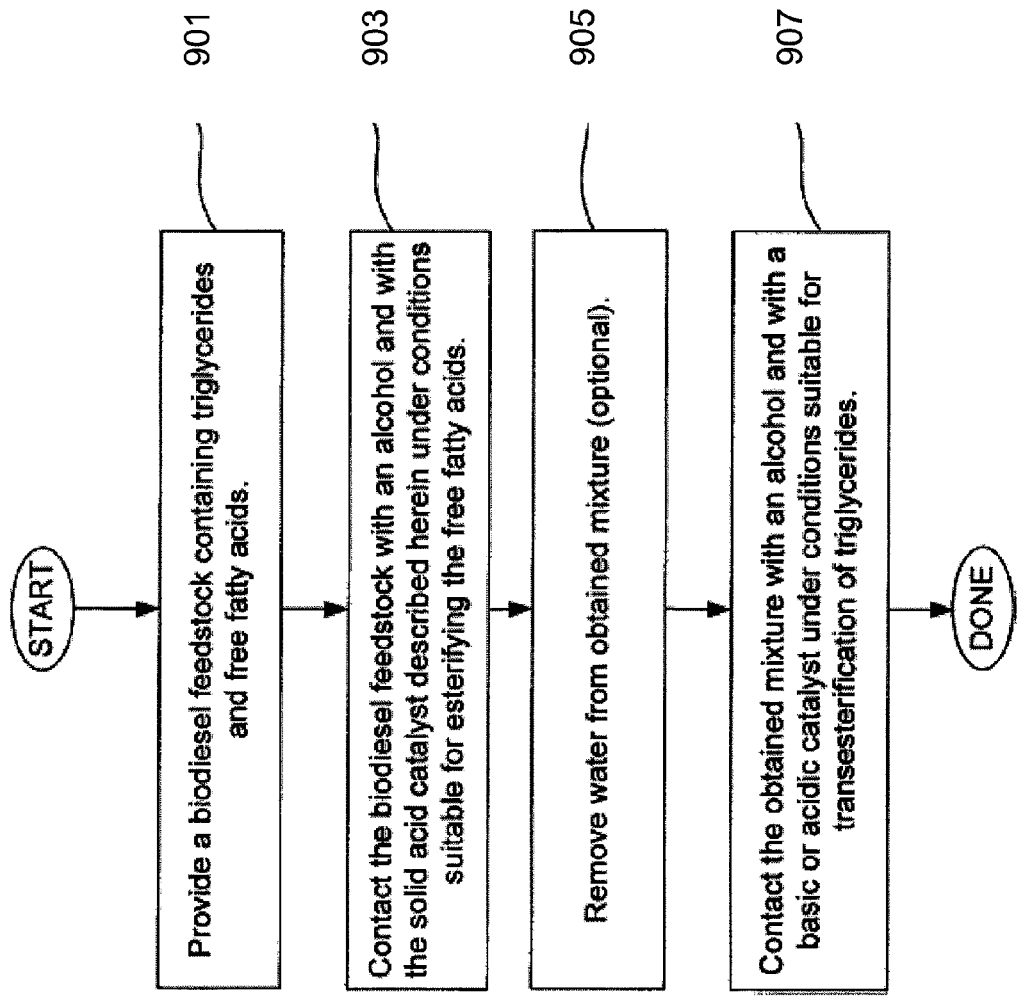
FIG. 9 is an exemplary process flow diagram for a method of processing a biodiesel feedstock in accordance with certain embodiments described herein.

In one implementation, illustrated in FIG. 9, the present solid acid catalyst can be used for pre-esterification of FFAs in biodiesel feedstocks containing triglycerides and FFAs. Upon pre-esterification, subsequent transesterification of triglycerides to form glycerin and FFA esters (e.g., FFA methyl esters) can be carried out using homogeneous or heterogeneous basic or acidic catalysts known in the art, or alternatively, using the present solid acid catalysts. The illustrative process flow is shown in FIG. 9. The process includes providing a biodiesel feedstock containing triglycerides and free fatty acids in operation 901. For example, biodiesel feedstocks with FFA content of at least about 0.5% wt., e.g., at least about 5% wt. can be provided.

The feedstock is optionally dried, e.g., by heating under vacuum, and the process follows in 903 by contacting the biodiesel feedstock with an alcohol (e.g., ethanol or methanol) and with the present solid acid catalyst under conditions that are suitable for esterifying free fatty acids. For example, the mixture of biodiesel feedstock and alcohol may be passed over or through a fixed catalyst bed disposed in a reactor. In other embodiments, the reaction mixture may be contacted with the catalyst in granular or powder form. The esterification reaction is allowed to proceed at appropriate temperature and pressure. While often no co-solvents are used in the reaction mixture, in certain embodiments co-solvents, such as tetrahydrofuran may be added to the feedstock to improve miscibility of alcohols and triglycerides. In other embodiments, the reaction mixture is primed in the beginning by addition of fatty acid methyl (or ethyl) ester to improve miscibility and to start the reaction.

Upon completion of FFA pre-esterification, water is optionally removed from the pre-processed feedstock in operation 905. In certain embodiments, water is removed by distillation along with excess alcohol. Next, the pre-processed feedstock is ready for transesterification, which is performed by any suitable transesterification method known in the art. As outlined in 907, transesterification is performed by contacting the obtained mixture with an alcohol (e.g., with methanol or ethanol) and with a basic or acidic catalyst under conditions that are suitable for transesterification of triglycerides. Suitable transesterification catalysts include without limitation basic catalysts such as sodium hydroxide, sodium methylate, and solid basic resins such as Amberlyst A26 (OH), as well as acidic catalysts, such as sulfonated zirconia, and solid acid catalysts disclosed herein.

In one specific embodiment, both pre-esterification of FFAs (operation 903) and subsequent transesterification (operation 907) are performed using the solid catalysts of the invention.

In certain embodiments transesterification and subsequent glycerin removal and isolation of biodiesel fuel is performed according to the methods described in the US Patent Application Publication 2008/0119664 titled "Optimized Biodiesel Reaction Kinetics System" by Sinoncelli et al., filed on Oct. 30, 2007, which is herein incorporated by reference in its entirety and for all purposes.

Use of the Present Solid Acid Catalysts for Glyceride Transesterification

Figure 10:
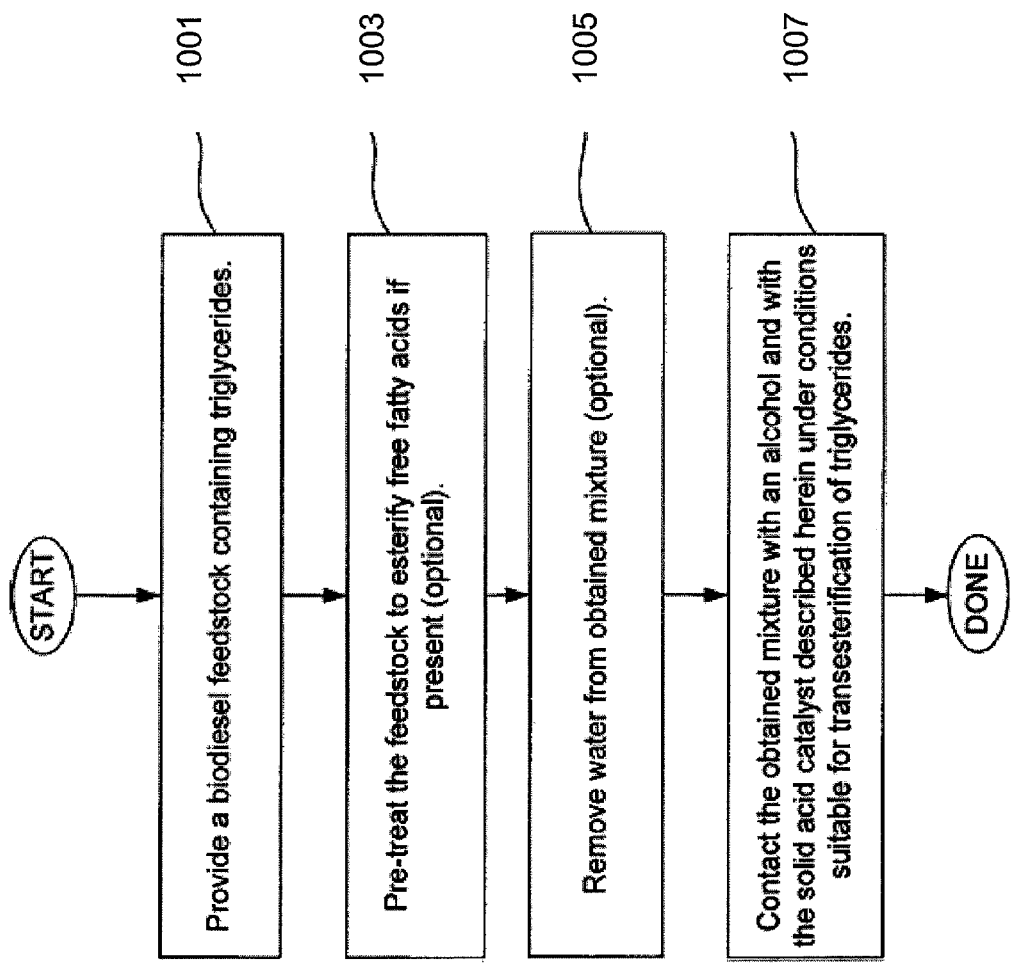
FIG. 10 is an exemplary process flow diagram for a method of processing a biodiesel feedstock in accordance with certain embodiments described herein.

An alternative biodiesel feedstock processing method, illustrated by process flow diagram of FIG. 10, uses the present solid acid catalyst for transesterification of triglycerides. This embodiment of the process need not use the present catalyst for FFA esterification. The process starts in 1001 by providing a biodiesel feedstock containing triglycerides. FFAs may or may not be present in this feedstock. If present in large quantities, FFAs may be optionally removed via pre-esterification, as shown in 1003. In this embodiment, pre-esterification may be performed by known methods, or by using the present solid acid catalyst. If needed, water is optionally removed after pre-esterification of FFAs in 1005, e.g., by distillation. In operation 1007, the mixture containing triglycerides is contacted with an alcohol (e.g., with methanol or ethanol) and with the present solid catalyst under conditions suitable for transesterification of triglycerides. As for pre-esterification of FFAs, the transesterification reaction mixture may be passed over or through a fixed bed of catalyst in a reactor, or can be mixed with catalyst powder or granules, which can be later removed by filtration. In certain embodiments, the transesterification reaction mixture can include co-solvents such as tetrahydrofuran. In an embodiment, no co-solvent is used. In such an embodiment, the reaction mixture can be initially primed by addition of fatty acid methyl (or ethyl) ester to improve miscibility of triglycerides with the alcohol. Removal of glycerin during or after transesterification can be performed using methods described in the US Patent Application Publication 2008/0119664 titled "Optimized Biodiesel Reaction Kinetics System" by Sinoncelli et al., previously incorporated by reference.

It is understood that transesterification of triglycerides is described as an illustration of one embodiment, and glycerides in general (such as mono- and di-glycerides) can be successfully esterified by the present method.

Esterification and Transesterification Reactor

In another aspect, the invention provides reactors configured for performing esterification and/or transesterification reactions which are loaded with the present solid acid catalyst. The present catalyst, in an embodiment, can be a in fixed catalyst bed which may completely or partially occupy the reactor chamber. In an embodiment, the catalyst can be within a reactor in the form of packed column.

In an embodiment, the reactor includes a reaction chamber, a layer of the present solid acid catalyst disposed on the reaction chamber wall. The reactor includes an entry port, which can be configured for introduction of starting materials (e.g., unprocessed or pre-processed biodiesel feedstocks) and an exit port configured for exit of esterified or transesterified reaction products.

It is understood that the reactors described above are only illustrations of possible reactor designs, and that a variety of alternative designs are possible. For example, the reactor may be configured for a continuous flow or a for a batch process; exit and entry ports can be configured to be closed when desired; and the reactor can be configured for performance under higher than atmospheric pressure. Further, in an embodiment, the reactor may have only one port, which may serve both for entry and exit of the reactant. Additionally, the present solid acid catalyst need not necessarily be disposed on the reactor walls, but may, for example, reside on a support within the reaction chamber. The reactor can include a controller adapted for controlling temperature and pressure within the reaction chamber, as well as flow rates of individual components of transesterification and esterification mixtures. In an embodiment, the reactor includes a design described in the US Patent Application Publication 2008/0104885 titled "Static Reactor System" by J. Sinoncelli, filed on Sep. 13, 2007, which is herein incorporated by reference.

Other Reactions

The above list of acid-catalyzed reactions catalyzed by the present solid acid catalyst is illustrative, but not exhaustive. It is understood that a variety of other acid-catalyzed reactions known to be catalyzed by conventional solid acids can be catalyzed by the present solid acid catalyst.

Examples of these other reactions include without limitation dimerization of olefin, bicyclic hydrocarbon isomerization, dimerization for high density fuel production, ester hydrolysis reactions, reactions related to protection and deprotection of various functional groups, such as tetrahydropyranylation of alcohols and acetalization of carbonyl compounds; bis-hydroxylation of alkenes to yield 1,2-diols; glycosylation reaction and ortho-Claisen rearrangement; epoxide ring opening; polymerization of cyclic ethers (e.g., THF); and nitration of aromatic substrates.

Examples of such reactions are disclosed in described in US Patent Application Publication No. 2006/0046925 by Schlitter et al., published on Mar. 2, 2006; in US Patent Application Publication 2004/0024267 by Dongare et al. published on Feb. 5, 2004; and in US Patent Application 2009/0099400 titled "Solid Phosphoric acid catalyst and method of olefins dimerization reaction with the same" by Tatsuo Hamamatsu e o. filed on May 25, 2006. Each of these published patent applications is incorporated herein by reference.

The present invention may be better understood with reference to the following examples. These examples are intended to be representative of specific embodiments of the invention, and are not intended as limiting the scope of the invention.

EXAMPLES

Four solid acid catalysts in accordance with embodiments described herein were prepared and were tested in an esterification reaction. Commercially available SAC-13 catalyst, prepared $WO_3/ZrO_2$ catalyst, and prepared glucose-based sulfonated carbon were used as comparative examples.

Preparation of Catalyst 1

1.58 g of Dow Novolac epoxy resin DEN 438-A85 (partially polymerized phenol-formaldehyde resin) was mixed with 0.16 ml ethyl acetate (EA). This solution was then mixed with 0.075 ml of 65 wt % solution 2-ethyl-4-methylimidazole (EMI) in ethyl acetate. Next, 1 g of Water Resistant Silica Gel (available from SilicaStar Industries, Fremont, Calif.) was added to the solution. Material was mixed thoroughly and was left for 30 min.

Next, a vial with formed material was placed into tubular oven and was heated under nitrogen flow according to flowing program: 3 minutes heating to 120° C., temperature hold for 2 hr, 5 minutes heating to 400° C., temperature hold for 4 hrs. The carbonized material was cooled to room temperature and coke (carbon) amount was calculated from the weight after carbonization. The amount of coke refers to the amount measured prior to sulfonation. The carbonized material was treated with 15 ml of 96% $H_2SO_4$ at 150° C. for 4 hours. Next, the resulting solid was filtered and was washed with deionized water having 80° C. temperature until no sulfate ions were detected in the washes by reaction with barium nitrate (wash at least 7 times). Washed material was dried under vacuum at 80° C. for 2 hours.

Preparation of Catalyst 2

1.54 g CVC Bisphenol epoxy resin EPALLOY 7190-A83 was mixed with 0.15 ml ethyl acetate. This solution was mixed with 0.075 ml of 65 wt % solution 2-ethyl-4-methylimidazole in ethyl acetate and 1 g of MA 1620 silica (available from PQ corporation) for impregnation was added to the solution. Subsequent processing was the same as for catalyst 1.

Preparation of catalysts 3 and 4.

Catalysts 3 and 4 were prepared similarly to catalysts 1 and 2. Types of used materials and amounts of reagents are listed in Table 1.

TABLE 1

Preparation of Catalysts

| Catalyst | $SiO_2$ | Resin | Resin (g) | EA (ml) | EMI sol. (µl) | Coke (wt %) | Sulfur (wt %) |
|---|---|---|---|---|---|---|---|
| 1 | Silicastar | DEN 438-A85 | 1.58 | 0.16 | 75 | 32.3 | 3.48 |
| 2 | M 1620 | EPALLOY 7190-A83 | 1.54 | 0.15 | 75 | 20.5 | 2.44 |
| 3 | M 1620 | DEN 438-A85 | 1.53 | 0.15 | 60 | 30.5 | 3.59 |
| 4 | Silicastar | DEN 438-A85 | 1.55 | 0.16 | 60 | 29.7 | 3.4 |

Sulfur percentage was measured by combustion method (Galbraith).

SAC-13 (Comparative Catalyst)

Commercially available catalyst SAC-13 was used for comparison in activity measurements.

$WO_3/ZrO_2$ Comparative Catalyst)

Another comparative catalyst (10% wt $WO_3/ZrO_2$) was prepared by the following procedure. 1 g of high purity $ZrO_2$ (Saint Gobain, XZ 16122, BET=135 m²/g, fraction 40-80 mesh) was impregnated with 0.5 ml solution of ammonium metatungstate (GERAC, concentration 0.96 M W) to give 10% wt $WO_3$. Impregnated material was dried at 110° C. for 4 hours and was heated at 800° C. for 3 hours. This procedure provides maximal acidity of material. The prepared comparative catalyst 6 was in activity measurements.

Catalyst 5 (Comparative Catalyst)

2.867 g of glucose (Aldrich) was mixed with 1.3 ml of DI water and was heated at 50° C. to complete dissolution. 1 g $SiO_2$ (PQ corp., BET=237 m²/g, APS=195 Å, PPS=450 Å) was impregnated with 1 ml of this solution. After that vial with material was placed into tubular oven and was heated under nitrogen flow under the same conditions as Catalyst 1. Coke amount was calculated after cooling material to room temperature and amounted to 17.7 wt %. Next, the material was treated with sulfuric acid under the same conditions as Catalyst 1. Resulting material has BET=234 m²/g, APS=190 Å, PPS=450 Å).

Characterization of Supports and Catalysts

Figure 11:
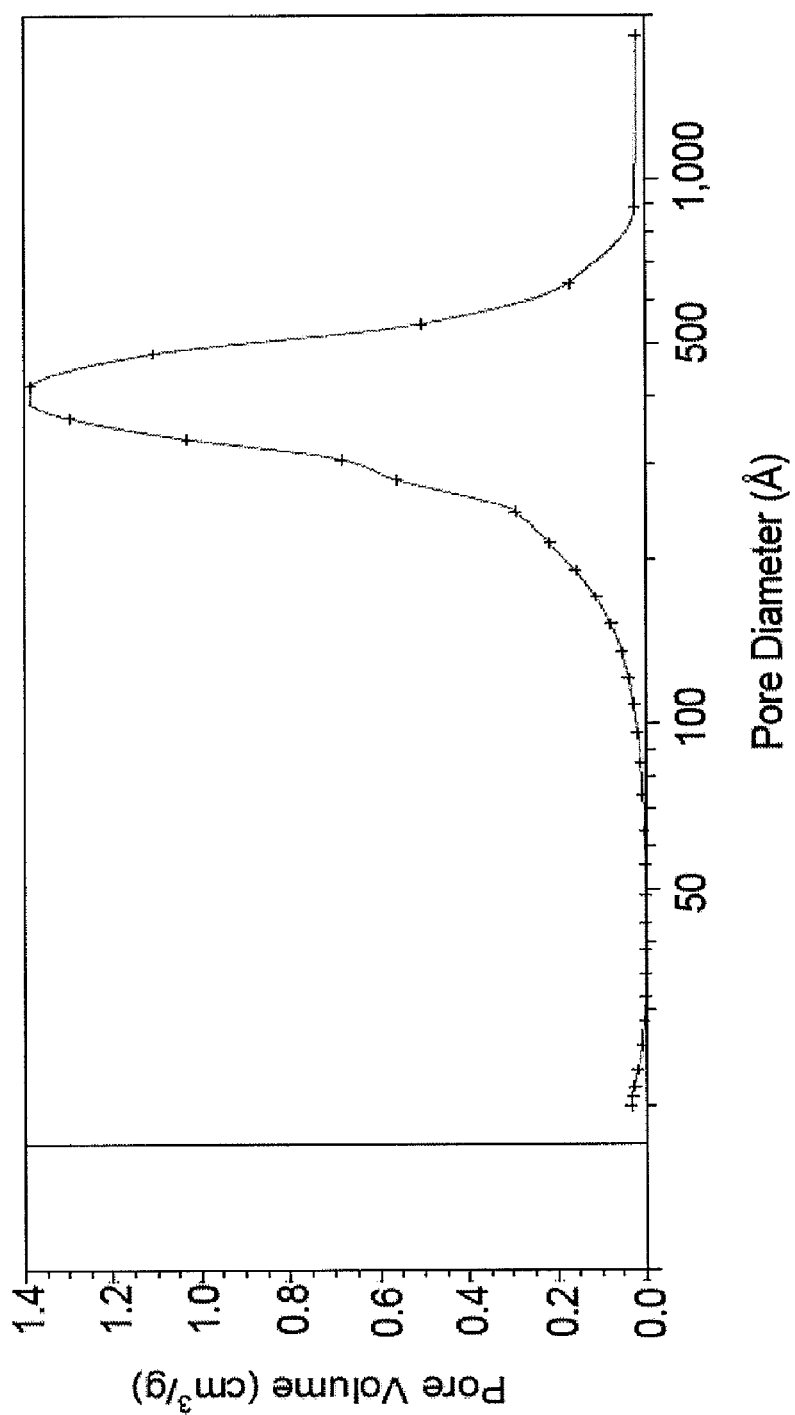
FIG. 11 is an experimental plot illustrating pore size distribution in one embodiment of the present solid acid catalyst.

BET values and pore size distribution for supports and catalysts were measured on TriSTAR 3000 gas adsorption analyzer (Micromeritics, USA). Table 2 below shows BET values, average pore size (APS), and predominant pore size at maximum distribution (PPS) for the catalysts and their supports. A pores size distribution curve for Catalyst 2 is shown in FIG. 11.

TABLE 2

Textural properties of supports and catalysts

| | Support | | | Catalyst | | |
|---|---|---|---|---|---|---|
| Catalyst | BET (m²/g) | APS (Å) | PPS (Å) | BET (m²/g) | APS (Å) | PPS (Å) |
| Catalyst 1 | 115 | 177 | 500 | 72 | 216 | 500 |
| Catalyst 2 | 194 | 205 | 450 | 190 | 232 | 400 |
| Catalyst 3 | 194 | 205 | 450 | 105 | 287 | 400 |
| Catalyst 4 | 115 | 177 | 500 | 104 | 373 | 500 |

Activity Measurements

Most of the activity tests were performed in a lauric acid esterification reaction with methanol which was conducted at 80° C. for 2 hours in a high pressure high throughput reactor, at a pressure of about 2 atmospheres. A plate with a set of 4 ml reaction vessels (Kimble Chase, 15×44 OD), insulated by silicon gasket was placed into pressure vessel, which was shaken at 500 rpm to provide sufficient mixing inside reaction vessels. Activity of every catalyst was measured in 3-4 reactors in parallel. Every reaction vessel contained 2.5 ml of methanol, about 300 mg FFA and from 5 to 20 mg of catalysts. High temperature experiments were performed in an autoclave with 20 ml of methanol and 2.4 g FFA. After the reaction was completed, the reaction mixture was analyzed using gas chromatography (GC) with an ALLTECH FEMA column, and FFA conversions were calculated for each catalyst.

Because a very high $CH_3OH/FFA$ ratio was used in these experiments (~40), activity was calculated as a rate constant of a first order reaction according to the following equation:

$$\ln(1-X) = k \cdot t,$$

where X is FFA conversion; t is reaction time, and k is the rate constant.

To take into account difference in catalyst loading, and reactor volume, activity was calculated as an overall rate constant divided by catalyst amount and multiplied by reactor volume.

All catalysts were tested in a high throughput reactor at 80° C. for 2 hours. Average activity (Activity, mL/hours·g) and standard deviation for each catalyst are shown in Table 3.

TABLE 3

Catalyst Activities in an Esterification Reaction and Catalyst's H⁺ Concentrations

| Catalyst | Activity (mL/hours · g) | Std. Dev. | H⁺ (mmol/g) |
|---|---|---|---|
| Catalyst 1 | 171.4 | 20.2 | 1.09 |
| Catalyst 2 | 193.8 | 40.3 | 0.76 |
| Catalyst 3 | 203.0 | 16.8 | 1.12 |
| Catalyst 4 | 160.4 | 34.7 | 1.06 |
| SAC-13 | 51.7 | 7.1 | 0.15 |
| 10 wt-% $WO_3/ZrO_2$ | 0.24 | 0.055 | — |
| Catalyst 5 (comparative) | 34.4 | 6.5 | n/a |

Density of H⁺ sites was calculated based on sulfur content that was previously obtained by combustion method, assuming there is one sulfur atom per each —$SO_3H$ group.

It can be seen that phenol-based catalysts 1-4 showed significantly higher activities than conventional SAC-13 and $WO_3/ZrO_2$ catalysts, and greater activity than comparative glucose-based catalyst 5. Formation of an extended, phenol-containing polymeric network is believed to increase the binding of resulting sulfonated carbon to silica, in comparison to glucose-derived sulfonated carbon, which is relatively weakly bound to silica support and can be more easily washed out during the reaction. Further, the present phenol-derived catalysts are more advantageous than glucose-derived catalysts. Although not limiting to the present invention it is believe that, upon partial carbonization, the present solid acid catalysts provide a larger aromatic network that is more amenable to sulfonation than pyrolyzed glucose.

Catalyst Stability Test

Catalysts 1 and 2 were used in a stability test. The catalysts were heated in the mixture of methanol and lauric acid at 120° C. for 12 hours. Upon heating, the reaction mixture was removed, catalysts were washed with methanol, and the activity test was performed. Activity was measured as described above in a reaction of lauric acid with methanol performed at 80° C. for two hours.

In a separate experiment, catalysts 1 and 2 were heated in the mixture of methanol and lauric acid at 150° C. for 12 hours, and their activities were subsequently measured as described above.

For comparison, identical stability tests were performed with SAC-13. The results are presented in Table 4.

TABLE 4

Activities of catalysts (mL/hours · g)

| | Catalyst 1 | Catalyst 2 | SAC-13 |
|---|---|---|---|
| Initial Activity | 171.4 | 193.8 | 51.5 |
| Std. Dev. | 20.2 | 40.3 | 6.7 |
| After 120° C., 12 h | 53.8 | 91.8 | 12.3 |
| Std. Dev. | 6.7 | 16.2 | 5.3 |
| After 50° C., 12 h | 54.9 | 48.2 | 11.8 |
| Std. Dev. | 8.1 | 9.5 | 7.3 |

High Temperature Test

The high temperature test was preformed with a larger reaction mixture volume in a Parr autoclave (75 ml with titanium stirrer). 20 ml of methanol were mixed with 2.48 g of lauric acid and 12.9 mg of catalyst 4 was added. The reaction was carried out for 1 hr at 120° C. After one hour, the autoclave was cooled down and the mixture was analyzed. Activity was calculated as described previously. Results are presented in Table 5.

For comparison, a similar high temperature test was performed with SAC-13. In this case 22.2 mg of SAC-13 catalyst, 20 ml of methanol and 2.45 g of lauric acid were used. Results are also shown in Table 5.

TABLE 5

Activities of catalysts in a high-temperature test (120° C., MeOH/lauric acid = 40)

| Catalyst | Activity (mL/hours · g) |
|---|---|
| Catalyst 4 | 1580 |
| SAC-13 | 90 |

The results presented above show that embodiments of the present solid acid catalysts demonstrated activities that were 3-4 times higher than SAC-13 activity at 80° C. The present solid acid catalysts have good textural properties and have high density of acid sites (5-7 times higher than SAC-13). An EPALLOY based material (Catalyst 2) had less coke and higher surface area than DEN based materials. It also had a slightly lower concentration of sulfonic groups. DEN based materials (Catalysts 1, 3, 4) had more coke and have higher sulfonic group concentration, which correlated among these materials with their activity. At higher temperature, advantages of the present solid acid catalysts over conventional SAC-13 catalyst were even more pronounced: at 120° C. activity of Catalyst 4 was more than 10 times greater than activity of SAC-13.

It is understood that the examples and embodiments described herein are for illustrative purposes only and that various modifications or changes in light thereof can be made. Although various details have been omitted for clarity's sake, various design alternatives may be implemented. Therefore, the present examples are to be considered as illustrative and not restrictive, and the invention is not to be limited to the details given herein, but may be modified within the scope of the appended claims.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

The invention claimed is:

1. A porous solid acid catalyst, the catalyst comprising:
    (a) a support comprising a porous silica network; and
    (b) a sulfonated carbon layer residing within the porous silica network;
wherein the solid acid catalyst has a concentration of —SO3H groups of at least about 0.5 mmol/g and a predominant pore size of at least about 300 Å.

2. The solid acid catalyst of claim 1, prepared by a method comprising:
    (a) impregnating a porous silica support with a phenol-containing material;
    (b) processing the phenol-containing material to form a polymer containing aromatic groups, wherein the polymer resides within the pores of the porous silica support;
    (c) carbonizing the polymer by heat treatment in a non-oxidizing atmosphere; and
    (d) treating the obtained carbonized partially prepared catalyst with a sulfonating agent to form a sulfonated carbon layer within the porous silica support.

3. The method of claim 2, wherein the phenol-containing material comprises a phenol-containing monomer, oligomer, or polymer (resin).

4. The method of claim 3, wherein:
    the phenol-containing resin is a phenol-formaldehyde epoxy resin; and
    processing the phenol-formaldehyde epoxy resin comprises forming a cross-linked polymer.

5. The method of claim 3, wherein the phenol-formaldehyde epoxy resin comprises phenol or bisphenol.

6. The method of claim 3, wherein (a) and (b) comprise:
    contacting the porous silica support with a phenol-formaldehyde epoxy resin and curing the resin with a curing agent or by heating.

7. A method for performing an acid-catalyzed reaction, the method comprising:
    (a) contacting a starting material of an acid-catalyzed reaction with a porous solid acid catalyst of claim 1;
    (b) allowing the acid-catalyzed reaction to proceed for a period of time to form a product of the reaction; and
    (c) collecting the formed product.

8. The method of claim 7, wherein:
    the acid-catalyzed reaction is an alkane/alkene alkylation; and
    (a) comprises contacting the solid acid catalyst with a starting material comprising an alkane and an alkene.

9. The method of claim 7, wherein:
    the acid-catalyzed reaction is a Friedel-Crafts alkylation; and
    the starting material comprises an aromatic compound and an alkylating agent.

10. The method of claim 7, wherein:
    the acid-catalyzed reaction is a Friedel-Crafts acylation; and
    the starting material comprises an aromatic compound and an acylating agent.

11. The method of claim 7, wherein:
    the acid-catalyzed reaction is an etherification reaction; and
    the starting material comprises a first starting material selected from the group consisting of an olefin and an alcohol and a second starting material comprising an alcohol.

12. The method of claim 7, wherein:
    the acid-catalyzed reaction is olefin hydration;
    the starting material comprises an olefin and water; and
    the product comprises an alcohol.

13. The method of claim 7, wherein the acid catalyzed reaction is bicyclic hydrocarbon dimerization.

14. The method of claim 7, wherein:
    the acid-catalyzed reaction is olefin dimerization; and
    the starting material comprises an olefin.

15. The catalyst of claim 1, wherein the catalyst is active in catalyzing esterification of a fatty acid with a monohydric alcohol.

16. The catalyst of claim 1, wherein the catalyst exhibits less than about 20% volumetric increase upon exposure to a liquid esterification reaction mixture for 12 hours at 80° C.

17. The catalyst of claim 1, wherein the catalyst is active in catalyzing transesterification of a triglyceride contained in a fat or in an oil with methanol or ethanol.

18. A method for processing a biodiesel feedstock comprising a triglyceride and a free fatty acid (FFA), the method comprising:
    (a) contacting the feedstock with a monohydric alcohol and a first catalyst under conditions suitable for esterification of the free fatty acid, wherein the first catalyst is a solid acid catalyst of claim 1;

(b) contacting the mixture obtained after (a) with a monohydric alcohol and with a second catalyst under conditions suitable for transesterification of the triglyceride.

19. The method of claim 18, wherein the second catalyst is a porous solid acid catalyst comprising:
   a support comprising a porous silica network; and
   a sulfonated carbon layer residing within the porous silica network,
   wherein the solid acid catalyst has a concentration of —SO3H groups of at least about 0.5 mmol/g, and a predominant pore size at maximum distribution of at least about 300 Å.

* * * * *